(12) United States Patent
Goldberg et al.

(10) Patent No.: US 11,273,062 B2
(45) Date of Patent: Mar. 15, 2022

(54) EXPANDABLE SHEATH

(71) Applicant: Edwards Lifesciences Corporation, Irvine, CA (US)

(72) Inventors: Eran Goldberg, Nesher (IL); Noa Axelrod, Netanya (IL); Yair A. Neumann, Moshav Sede Varburg (IL); Boaz Manash, Givat Ada (IL); David Maimon, Atlit (IL); Eyal Leiba, D.N. Misgav (IL); Ralph Schneider, Trabuco Canyon, CA (US); Liron Tayeb, Peduel (IL)

(73) Assignee: Edwards Lifesciences Corporation, Irvine, CA (US)

( * ) Notice: Subject to any disclaimer, the term of this patent is extended or adjusted under 35 U.S.C. 154(b) by 186 days.

(21) Appl. No.: 16/378,417

(22) Filed: Apr. 8, 2019

(65) Prior Publication Data

US 2019/0307589 A1 Oct. 10, 2019

Related U.S. Application Data

(60) Provisional application No. 62/722,958, filed on Aug. 26, 2018, provisional application No. 62/655,059, filed on Apr. 9, 2018.

(51) Int. Cl.
*A61F 2/966* (2013.01)
*A61M 25/00* (2006.01)
(Continued)

(52) U.S. Cl.
CPC ............ *A61F 2/966* (2013.01); *A61F 2/2436* (2013.01); *A61F 2/9526* (2020.05);
(Continued)

(58) Field of Classification Search
CPC ................ A61M 25/005; A61M 25/10; A61M 25/10184; A61M 25/0012;
(Continued)

(56) References Cited

U.S. PATENT DOCUMENTS 4,601,713 A 7/1986 Fuqua
4,710,181 A 12/1987 Fuqua
(Continued)

FOREIGN PATENT DOCUMENTS

EP 0103546 A1 3/1984
EP 0592410 B1 10/1995
(Continued)

OTHER PUBLICATIONS

510K Premarket Notification, Jun. 22, 2018.
BSX Structural Heart Update 2018.

*Primary Examiner* — Richard G Louis
(74) *Attorney, Agent, or Firm* — Meunier Carlen Curfman LLC; Joel B. German

(57) ABSTRACT

An expandable sheath is disclosed herein, which has a first polymeric layer and a braided layer positioned radially outward of the first polymeric layer. The braided layer includes a plurality of filaments braided together. The expandable sheaths further include a resilient elastic layer positioned radially outward of the braided layer. The elastic layer is configured to apply radial force to the braided layer and the first polymeric layer. The expandable sheath further includes a second polymeric layer positioned radially outward of the elastic layer and bonded to the first polymeric layer such that the braided layer and the elastic layer are encapsulated between the first and second polymeric layers. Methods of making and using the devices disclosed herein are also disclosed, as are crimping devices that may be used in methods of making the devices disclosed herein.

28 Claims, 21 Drawing Sheets

(51) Int. Cl.
*B29D 23/00* (2006.01)
*A61F 2/24* (2006.01)
*A61F 2/95* (2013.01)
*A61F 2/958* (2013.01)
*B29K 105/08* (2006.01)
*A61M 29/00* (2006.01)
*A61F 2/962* (2013.01)

(52) U.S. Cl.
CPC .... *A61M 25/0012* (2013.01); *A61M 25/0023* (2013.01); *B29D 23/00* (2013.01); *A61F 2/9517* (2020.05); *A61F 2/9522* (2020.05); *A61F 2002/9583* (2013.01); *A61F 2002/9623* (2020.05); *A61F 2002/9665* (2013.01); *A61F 2250/001* (2013.01); *A61M 25/005* (2013.01); *A61M 25/0045* (2013.01); *A61M 25/0074* (2013.01); *A61M 29/00* (2013.01); *A61M 2025/0024* (2013.01); *A61M 2205/0216* (2013.01); *B29K 2105/0827* (2013.01)

(58) Field of Classification Search
CPC .......... A61M 25/0023; A61M 25/0045; A61M 25/0074; A61M 29/00; A61M 2025/0024; A61M 2205/0216; A61B 17/1204; A61F 2/966; A61F 2/2436; A61F 2/9517; A61F 2/9522; A61F 2002/9583; A61F 2002/9623; A61F 2002/9665; A61F 2250/001; A61F 2/243; B29D 23/00; B29K 2105/0827
See application file for complete search history.

(56) References Cited

U.S. PATENT DOCUMENTS

| | | | |
|---|---|---|---|
| 4,738,666 A | 4/1988 | Fuqua | |
| 4,921,479 A | 5/1990 | Grayzel | |
| 5,104,388 A | 4/1992 | Quackenbush | |
| 5,178,158 A * | 1/1993 | de Toledo | A61M 25/0053 600/434 |
| 5,318,588 A | 6/1994 | Horzewski et al. | |
| 5,320,611 A | 6/1994 | Bonutti et al. | |
| 5,501,667 A | 3/1996 | Verduin, Jr. | |
| 5,674,240 A | 10/1997 | Bonutti et al. | |
| 5,810,776 A | 9/1998 | Bacich et al. | |
| 5,817,100 A | 10/1998 | Igaki | |
| 5,997,508 A | 12/1999 | Lunn et al. | |
| 6,080,141 A | 6/2000 | Castro et al. | |
| 6,090,072 A | 7/2000 | Kratoska et al. | |
| 6,090,136 A | 7/2000 | McDonald et al. | |
| 6,190,357 B1 | 2/2001 | Ferrari et al. | |
| 6,312,443 B1 | 11/2001 | Stone | |
| 6,322,586 B1 * | 11/2001 | Monroe | A61F 2/95 606/108 |
| 6,346,092 B1 | 2/2002 | Leschinsky | |
| 6,358,238 B1 | 3/2002 | Sherry | |
| 6,443,979 B1 | 9/2002 | Stalker et al. | |
| 6,494,860 B2 | 12/2002 | Rocamora et al. | |
| 6,554,820 B1 * | 4/2003 | Wendlandt | A61M 25/005 604/527 |
| 6,632,236 B2 | 10/2003 | Hogendijk | |
| 6,652,492 B1 | 11/2003 | Bell et al. | |
| 6,814,715 B2 | 11/2004 | Bonutti et al. | |
| 6,899,727 B2 | 5/2005 | Armstrong et al. | |
| 7,438,712 B2 | 10/2008 | Chouinard | |
| 7,591,832 B2 | 9/2009 | Eversull et al. | |
| 7,655,016 B2 | 2/2010 | Demarais et al. | |
| 7,678,128 B2 | 3/2010 | Boyle et al. | |
| 7,713,193 B2 | 5/2010 | Nance et al. | |
| 7,762,995 B2 | 7/2010 | Eversull et al. | |
| 7,766,820 B2 | 8/2010 | Core | |
| 7,780,692 B2 | 8/2010 | Nance et al. | |
| 7,785,360 B2 | 8/2010 | Freitag | |
| 7,837,692 B2 | 11/2010 | Mulholland et al. | |
| 7,892,203 B2 | 2/2011 | Lenker et al. | |
| 7,927,309 B2 | 4/2011 | Palm | |
| 7,963,952 B2 | 6/2011 | Wright, Jr. et al. | |
| 8,034,072 B2 | 10/2011 | Nguyen et al. | |
| 8,048,034 B2 | 11/2011 | Eversull et al. | |
| 8,090,936 B2 | 1/2012 | Fallon et al. | |
| 8,092,481 B2 | 1/2012 | Nance et al. | |
| 8,252,015 B2 | 8/2012 | Leeflang et al. | |
| 8,282,664 B2 | 10/2012 | Nance et al. | |
| 8,414,645 B2 | 4/2013 | Dwork et al. | |
| 8,562,559 B2 | 10/2013 | Bishop et al. | |
| 8,562,673 B2 | 10/2013 | Yeung et al. | |
| 8,652,203 B2 | 2/2014 | Quadri et al. | |
| 8,668,668 B2 | 3/2014 | Bishop et al. | |
| 8,690,936 B2 | 4/2014 | Nguyen et al. | |
| 8,790,387 B2 | 7/2014 | Nguyen et al. | |
| 9,044,577 B2 | 6/2015 | Bishop et al. | |
| 9,192,751 B2 | 11/2015 | Macaulay et al. | |
| 9,192,752 B2 | 11/2015 | Leeflang et al. | |
| 9,254,374 B2 | 2/2016 | Thorstenson et al. | |
| 9,259,813 B2 | 2/2016 | Heideman et al. | |
| 9,301,840 B2 | 4/2016 | Nguyen et al. | |
| 9,301,841 B2 | 4/2016 | Nguyen et al. | |
| 9,320,508 B2 | 4/2016 | Carroux | |
| 9,393,041 B2 | 7/2016 | Barker et al. | |
| 9,642,704 B2 | 5/2017 | Tuval et al. | |
| 9,788,944 B2 | 10/2017 | Daly et al. | |
| 9,907,931 B2 | 3/2018 | Birmingham et al. | |
| 2001/0029378 A1 * | 10/2001 | Blaeser | A61F 2/958 606/108 |
| 2002/0007156 A1 * | 1/2002 | Miles | A61M 39/24 604/246 |
| 2002/0032459 A1 | 3/2002 | Horzewski et al. | |
| 2002/0123793 A1 | 9/2002 | Schaldach et al. | |
| 2003/0004537 A1 | 1/2003 | Boyle et al. | |
| 2003/0125710 A1 * | 7/2003 | Pepin | A61M 25/0045 604/525 |
| 2004/0087968 A1 | 5/2004 | Core | |
| 2004/0106942 A1 * | 6/2004 | Taylor | A61B 17/3462 606/185 |
| 2004/0122415 A1 | 6/2004 | Johnson | |
| 2004/0176740 A1 * | 9/2004 | Chouinard | A61M 25/0012 604/527 |
| 2005/0042448 A1 * | 2/2005 | Bullen | B32B 25/14 428/375 |
| 2005/0080430 A1 | 4/2005 | Wright et al. | |
| 2005/0085842 A1 | 4/2005 | Eversull et al. | |
| 2005/0125021 A1 | 6/2005 | Nance et al. | |
| 2006/0020321 A1 | 1/2006 | Parker | |
| 2006/0135962 A1 | 6/2006 | Kick et al. | |
| 2006/0135981 A1 * | 6/2006 | Lenker | A61M 25/0662 606/191 |
| 2006/0200110 A1 * | 9/2006 | Lentz | A61M 25/0662 604/524 |
| 2006/0217755 A1 | 9/2006 | Eversull et al. | |
| 2007/0021768 A1 | 1/2007 | Nance et al. | |
| 2007/0074805 A1 | 4/2007 | Leeflang et al. | |
| 2007/0087148 A1 | 4/2007 | Okushi et al. | |
| 2008/0004521 A1 | 1/2008 | Hundley et al. | |
| 2008/0004571 A1 | 1/2008 | Voss | |
| 2008/0082083 A1 * | 4/2008 | Forde | A61F 2/95 604/527 |
| 2008/0114331 A1 | 5/2008 | Holman et al. | |
| 2008/0243081 A1 | 10/2008 | Nance et al. | |
| 2008/0262472 A1 * | 10/2008 | Lunn | A61M 25/0012 604/527 |
| 2009/0234428 A1 * | 9/2009 | Snow | A61F 2/95 623/1.11 |
| 2010/0094209 A1 | 4/2010 | Drasler et al. | |
| 2010/0094392 A1 | 4/2010 | Nguyen et al. | |
| 2010/0198160 A1 | 8/2010 | Voss | |
| 2011/0112567 A1 | 5/2011 | Lenker et al. | |
| 2011/0190697 A1 | 8/2011 | Farnan | |
| 2011/0251681 A1 | 10/2011 | Shipley et al. | |
| 2012/0116439 A1 | 5/2012 | Ho | |
| 2012/0158033 A1 | 6/2012 | Deal et al. | |
| 2012/0323180 A1 | 12/2012 | Chebator et al. | |

(56) References Cited

U.S. PATENT DOCUMENTS

| | | |
|---|---|---|
| 2013/0131718 A1 | 5/2013 | Jenson et al. |
| 2013/0178711 A1 | 7/2013 | Avneri et al. |
| 2013/0231735 A1 | 9/2013 | Deem et al. |
| 2013/0281787 A1 | 10/2013 | Avneri et al. |
| 2014/0121629 A1 | 5/2014 | Macaulay et al. |
| 2014/0236122 A1 | 8/2014 | Anderson et al. |
| 2014/0236123 A1 | 8/2014 | Birmingham et al. |
| 2014/0276644 A1 | 9/2014 | Nelson |
| 2014/0379067 A1 | 12/2014 | Nguyen et al. |
| 2015/0119859 A1* | 4/2015 | Cajamarca ........ A61M 25/0012 604/526 |
| 2015/0182723 A1 | 7/2015 | Leeflang et al. |
| 2015/0238178 A1 | 8/2015 | Carroux |
| 2015/0265798 A1 | 9/2015 | Nihonmatsu et al. |
| 2015/0320971 A1 | 11/2015 | Leeflang et al. |
| 2016/0074067 A1 | 3/2016 | Furnish et al. |
| 2016/0135840 A1 | 5/2016 | Kick et al. |
| 2016/0213882 A1 | 7/2016 | Fitterer et al. |
| 2016/0296332 A1 | 10/2016 | Zhou et al. |
| 2016/0296730 A1 | 10/2016 | Zhou et al. |
| 2017/0014157 A1 | 1/2017 | Coyle et al. |
| 2017/0072163 A1 | 3/2017 | Lim et al. |
| 2017/0209133 A1 | 7/2017 | Ciulla et al. |
| 2017/0252062 A1 | 9/2017 | Fitterer et al. |
| 2018/0161064 A1 | 6/2018 | Fitterer et al. |
| 2018/0199960 A1 | 7/2018 | Anderson et al. |
| 2018/0229000 A1 | 8/2018 | Anderson et al. |

FOREIGN PATENT DOCUMENTS

| | | |
|---|---|---|
| EP | 1139889 A1 | 10/2001 |
| EP | 1694398 A2 | 8/2006 |
| EP | 1793881 A2 | 6/2007 |
| EP | 1804860 A2 | 7/2007 |
| EP | 2101661 A1 | 9/2009 |
| EP | 2288403 A2 | 3/2011 |
| EP | 2475417 A2 | 7/2012 |
| EP | 2862590 A1 | 4/2015 |
| EP | 2911729 A1 | 9/2015 |
| EP | 2995268 A1 | 3/2016 |
| JP | 2012040145 A | 3/2012 |
| WO | 2004037333 A1 | 5/2004 |
| WO | 2008147964 A1 | 12/2008 |
| WO | 2009035745 A1 | 3/2009 |
| WO | 2013044942 A1 | 4/2013 |
| WO | 2014140093 A1 | 9/2014 |
| WO | 2018148488 A1 | 8/2018 |

* cited by examiner

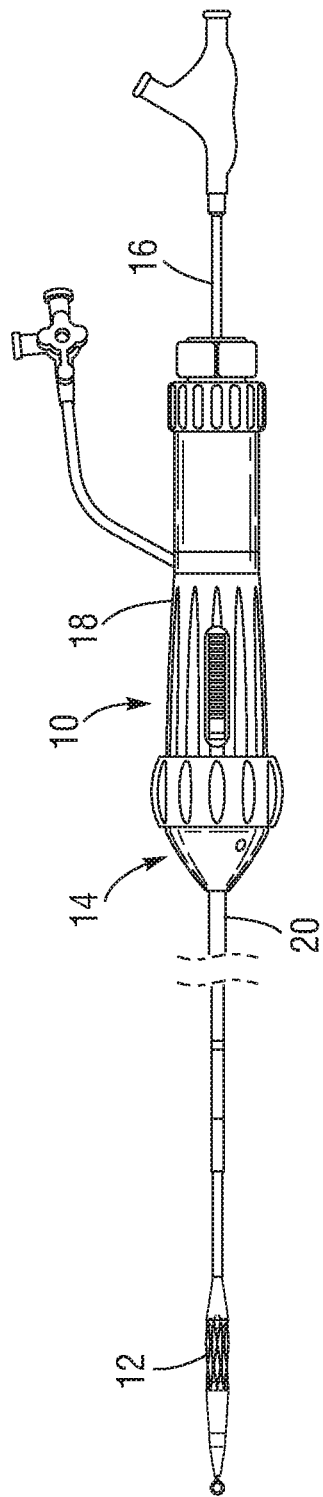
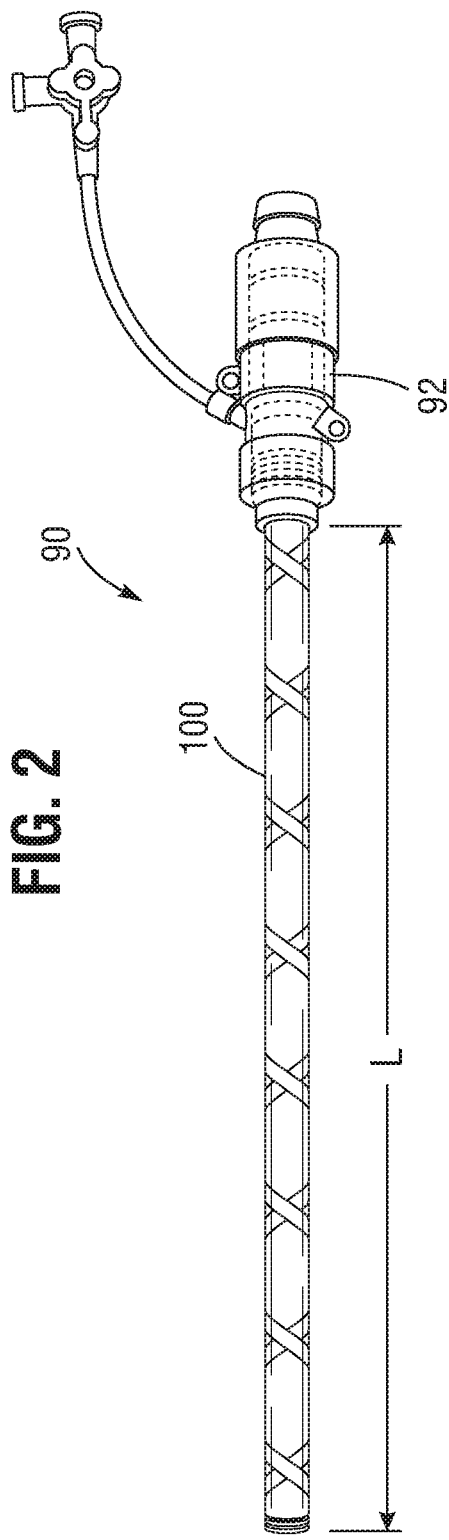

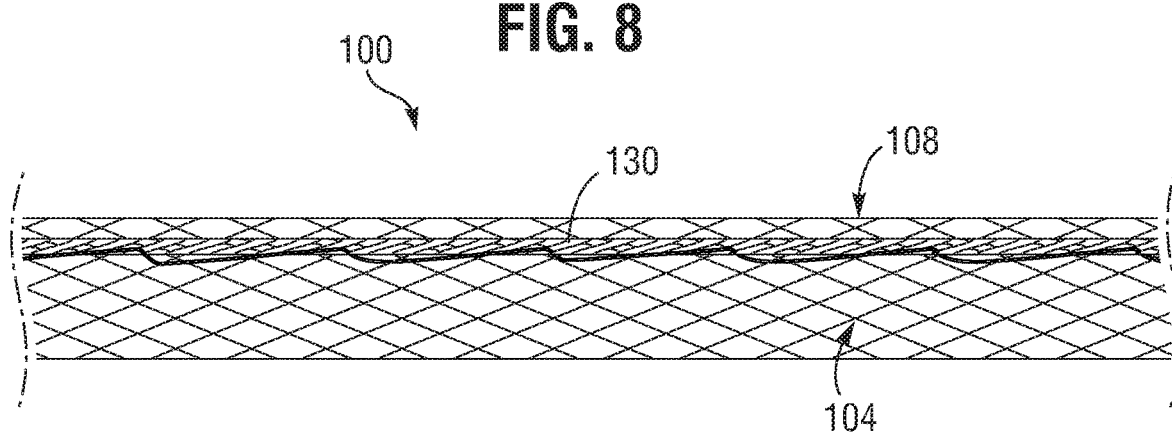
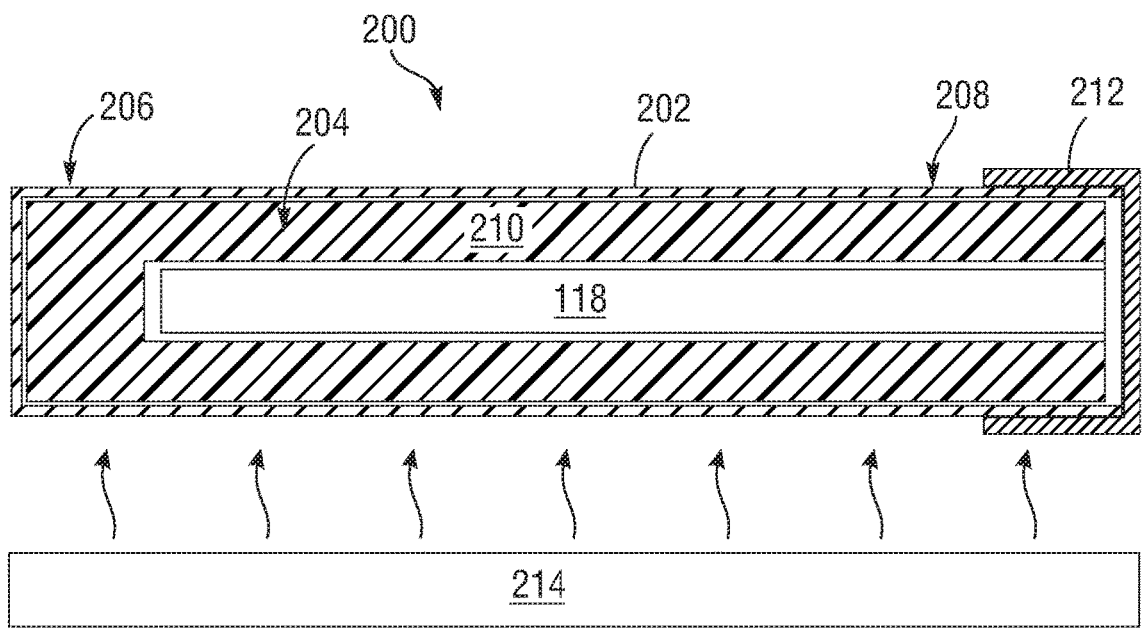

EXPANDABLE SHEATH

CROSS REFERENCE TO RELATED APPLICATIONS

This application claims the benefit of U.S. Provisional Applications 62/655,059, filed Apr. 9, 2018, and 62/722,958, filed Aug. 26, 2018. Each of these applications is incorporated by reference in their entireties for all purposes.

FIELD

The present application relates to expandable introducer sheaths for prosthetic devices such as transcatheter heart valves, and methods of making the same.

BACKGROUND

Endovascular delivery catheter assemblies are used to implant prosthetic devices, such as a prosthetic valve, at locations inside the body that are not readily accessible by surgery or where access without invasive surgery is desirable. For example, aortic, mitral, tricuspid, and/or pulmonary prosthetic valves can be delivered to a treatment site using minimally invasive surgical techniques.

An introducer sheath can be used to safely introduce a delivery apparatus into a patient's vasculature (e.g., the femoral artery). An introducer sheath generally has an elongated sleeve that is inserted into the vasculature and a housing that contains one or more sealing valves that allow a delivery apparatus to be placed in fluid communication with the vasculature with minimal blood loss. Such introducer sheaths may be radially expandable. However, such sheaths tend to have complex mechanisms, such as ratcheting mechanisms that maintain the sheath in an expanded configuration once a device with a larger diameter than the sheath's original diameter is introduced. Existing expandable sheaths can also be prone to axial elongation as a consequence of the application of longitudinal force attendant to passing a prosthetic device through the sheath. Such elongation can cause a corresponding reduction in the diameter of the sheath, increasing the force required to insert the prosthetic device through the narrowed sheath.

Accordingly, there remains a need in the art for an improved introducer sheath for endovascular systems used for implanting valves and other prosthetic devices.

SUMMARY

The expandable sheaths disclosed herein include a first polymeric layer and a braided layer positioned radially outward of the first polymeric layer. The braided layer includes a plurality of filaments braided together. The expandable sheaths further include a resilient elastic layer positioned radially outward of the braided layer. The elastic layer is configured to apply radial force to the braided layer and the first polymeric layer. The expandable sheaths disclosed herein further include a second polymeric layer positioned radially outward of the elastic layer and bonded to the first polymeric layer such that the braided layer and the elastic layer are encapsulated between the first and second polymeric layers. When a medical device is passed through the sheath, the diameter of the sheath expands from a first diameter to a second diameter around the medical device while the first and second polymeric layers resist axial elongation of the sheath such that a length of the sheath remains substantially constant. The sheath resiliently returns to the first diameter by radial force applied by the elastic layer upon passage of the medical device.

In some embodiments, the first and second polymeric layers include a plurality of longitudinally-extending folds when the sheath is at the first diameter. The longitudinally extending folds create a plurality of circumferentially spaced ridges and a plurality of circumferentially spaced valleys. As a medical device is passed through the sheath, the ridges and valleys level out to allow the sheath to radially expand.

The elastic layer can include one or more elastic bands helically wound over the braided layer. In some embodiments, two elastic bands are wound with opposite helicity.

As noted above, the braided layer is positioned radially outward of the first polymeric layer, but radially inward of the second polymeric layer. The filaments of the braided layer can be movable between the first and second polymeric layers such that the braided layer can radially expand as a medical device is passed through the sheath while the length of the sheath remains substantially constant, and, in some embodiments, the filaments of the braided layer are not engaged or adhered to the first or second polymeric layers at all. The filaments of the braided layer can also be resiliently buckled when the sheath is at the first diameter. In this embodiment, the first and second polymeric layers can be attached to each other at a plurality of open spaces between the filaments of the braided layer. Some embodiments can include one or more longitudinally extending cords attached to the braided layer.

An outer cover can extend longitudinally beyond the distal ends of the first polymeric layer, the braided layer, the elastic layer, and the second polymeric layer to form an overhang. In some embodiments, the outer cover comprises one or more longitudinally extending slits, weakened portions, or scorelines. In some embodiments, the outer cover is formed of a heat-shrink material. In some embodiments, the outer cover is elastomeric.

Methods of making expandable sheaths are also disclosed herein. The methods include: placing a braided layer radially outward of a first polymeric layer situated on a mandrel (the braided layer comprising a plurality of filaments braided together, the mandrel having a first diameter); applying an elastic layer radially outward of the braided layer (the elastic layer being configured to apply radial force to the first polymeric layer and the braided layer); applying a second polymeric layer radially outward of the elastic layer; applying heat and pressure to the first polymeric layer, the braided layer, the elastic layer, and the second polymeric layer (such that the first and second polymeric layers bond to each other and encapsulate the braided layer and the elastic layer to form an expandable sheath); and removing the expandable sheath from the mandrel to allow the expandable sheath to at least partially radially collapse to a second diameter that is less than the first diameter under radial force applied by the elastic layer.

In some embodiments, applying the elastic layer further comprises wrapping one or more elastic bands around the braided layer. The elastic bands can be applied in a stretched configuration. Or, after application of the braided layer, the first polymeric layer and braided layer can be removed from the mandrel, and the elastic layer can be applied in a relaxed or a moderately stretched state (after which the first polymeric layer, the braided layer, and the elastic layer are placed back on the mandrel to stretch the elastic layer prior to application of the second polymeric layer).

In some embodiments, the application of heat and pressure during the method of making the expandable sheath can be achieved by placing the mandrel in a vessel containing a thermally-expandable material, and heating the thermally-expandable material in the vessel. In some embodiments, a radial pressure of 100 MPa or more is applied to the mandrel via the thermally-expandable material. In some embodiments, applying heat and pressure further comprises applying a heat shrink tubing layer over the second polymeric layer and applying heat to the heat shrink tubing layer.

Some embodiments of the method of making the sheath include resiliently buckling the filaments of the braided layer of the sheath as the sheath is radially collapsed to the second diameter. Some embodiments include attaching one or more longitudinally extending cords to the braided layer to prevent axial elongation of the braided layer.

In some embodiments, an outer cover may be press fit into the removed expandable sheath such that the outer cover extends distally off distal ends of the first polymeric layer, the braided layer, the elastic layer, and the second polymeric layer at an overhang. The outer cover can be formed of a heat shrink tubing and/or it can be elastomeric.

The methods can further include crimping the expandable sheath to a third diameter, the third diameter being smaller than the first diameter and the second diameter. In some embodiments, the method of crimping the expandable sheath includes: supporting an inner surface of the entire length of the uncrimped sheath on an elongated mandrel having a conical end portion (the conical end portion nested within a narrowing lumen of a crimping mechanism); advancing the expandable sheath over the conical end portion and through the narrowing lumen while the uncrimped portion is supported by the mandrel; and compressing the sheath to the third, crimped diameter via pressure from an interior surface of the narrowing lumen of the crimping piece. In some embodiments, crimping the expandable sheath includes: contacting an end of the sheath with a plurality of radially arranged disc-shaped rollers, advancing the sheath through the plurality of disc-shaped rollers, and compressing the sheath to the third, crimped diameter via pressure from a circular edge of each disc-shaped roller as it rolls along an outer surface of the sheath. In some embodiments, crimping the expandable sheath includes: applying a first heat shrink tube to an outer surface of the sheath, compressing the sheath by shrinking the first heat shrink tube to an intermediate diameter, removing the first heat shrink tube, applying a second heat shrink tube to an outer surface of the sheath, compressing the sheath by shrinking the second heat shrink tube to a diameter smaller than the intermediate diameter, and removing the second heat shrink tube. Additional, consecutively smaller heat shrink tubes can be applied and shrunk until the sheath is compressed to the third diameter.

Methods of forming laminate products are also disclosed herein. The methods can include placing two or more layers of material inside a vessel so that the two or more layers of material are surrounded by a thermally-expandable material. Some embodiments include heating the thermally-expandable material in the vessel such that the thermally-expandable material expands and applies heat and pressure to the two or more material layers to form a laminate product. The methods can further include having the two or more layers of material positioned over a mandrel.

Assemblies are also disclosed herein. The assemblies can include the expandable sheath. The expandable sheath can also include a distal end portion resiliently expandable between the first diameter and a second diameter. Some embodiments include a vessel dilator disposed within the sheath. The vessel dilator can include a tapered nose cone and a retaining member that extends at least partially over the distal end portion of the sheath and is configured to retain the distal end portion of the sheath at the first diameter. In some embodiments, the distal end portion is heat-set toward an expanded configuration, and the elastic layer of the sheath terminates proximally of the distal end of the sheath. In some embodiments, a distal end portion of the braided layer is heat-set toward a flared configuration. In some embodiments the retaining member is a polymeric heat-shrink layer. In some embodiments the retaining member is elastomeric and configured to compress the distal end portion of the sheath. In some embodiments, the retaining member is glued or fused to the sheath. In some embodiments, the retaining mechanism includes a shaft disposed between the dilator and the sheath. In some embodiments the shaft includes a releasable coupling that mechanically engages both the dilator and the sheath that can be manually deactivated. In some embodiments the retaining mechanism can include one or more balloons disposed between the dilator and the sheath.

Methods of delivering a medical device are also disclosed herein. Methods of delivering a medical device, can include inserting an assembly into a blood vessel. The assembly can include a vessel dilator disposed within an expandable sheath. The vessel dilator can include a tapered nose cone. The expandable sheath can include a first polymeric layer, a braided layer radially outward of the first polymeric layer, a resilient elastic layer radially outward of the braided layer, and a second polymeric layer radially outward of the elastic layer. The methods can include withdrawing the vessel dilator through the sheath. The methods can include advancing a medical device through the sheath having a maximum diameter that is up to three times larger than the first diameter of the sheath. The methods can further include resisting axial elongation of the sheath as the medical device is advanced through the sheath such that the length of the sheath remains substantially constant. The methods can also include returning the sheath to the first diameter via radial force applied by the elastic layer. In some embodiments, inserting an assembly into a blood vessel further can include engaging the vessel dilator and the sheath by pressing the retaining member against the sheath. In some embodiments, advancing the vessel dilator distally of the sheath further can include breaking an adhesive bond between the retaining member and the sheath. The methods can include manually deactivating a releasable coupling that mechanically engages both the dilator and the sheath prior to advancing the vessel dilator distally of the sheath. The methods can include, further comprising deflating one or more balloons disposed between the dilator and the sheath prior to advancing the vessel dilator distally of the sheath.

In some embodiments, the vessel dilator can further include a retaining member configured to retain a distal end portion of the sheath at a first diameter. The methods can also include advancing the vessel dilator distally of the sheath such that the retaining member releases the distal end portion of the sheath, and the distal end portion of the sheath expands to a second diameter. In some embodiments, inserting an assembly into a blood vessel can include engaging the vessel dilator and the sheath by pressing an overhang portion of an outer cover of the sheath onto an outer surface of the vessel dilator. In some embodiments advancing a medical device through the sheath can include leveling out ridges and valleys created by a plurality of longitudinally extending folds. In some embodiments resisting axial elongation of the sheath can include straightening buckled filaments of the braided layer.

A crimping mechanism is also disclosed herein. A crimping mechanism can include a first end surface, a second end surface, and a longitudinal axis extending therethrough. The crimping mechanism can include a plurality of disc-shaped rollers radially arranged about the longitudinal axis. Each disc-shaped roller can have a circular edge, a first side surface, a second side surface, and a central axis extending between a center point of the first side surface and a center point of the second side surface, the plurality of disc-shaped rollers being oriented such that the central axes of the disc-shaped rollers each extend perpendicularly to the longitudinal axis of the crimping mechanism.

The crimping mechanism can include an axially extending passage extending along the longitudinal axis of the crimping mechanism and at least partially defined by the circular edges of the radially arranged plurality of disc-shaped rollers.

In some embodiments, each of the disc-shaped rollers are arranged at least partially between the first and second end surfaces of the crimping mechanism. In some embodiments, each of the disc-shaped rollers is held in the radially arranged configuration by a radially arranged plurality of connectors that are each attached to the crimping mechanism. In some embodiments, each of the radially arranged connectors comprises a first and second arm extending over a selected disc-shaped roller from the circular edge to a central portion of the disc-shaped roller, and a bolt attached to and extending between the first and second arms, the rod positioned loosely within a lumen defined between center points of the first and second side surfaces of the disc-shaped roller to allow the disc-shaped roller to rotate about the central axis of the disc-shaped roller. In some embodiments, each of the radially arranged connectors is attached to the crimping mechanism by one or more fasteners. In some embodiments, each of the disc-shaped rollers is held in the radially arranged configuration by a radially arranged plurality of connectors, the location of each of the plurality of connectors being fixed with respect to the first end surface of the crimping mechanism.

A device for crimping an elongated sheath is also included herein. The device for crimping an elongated sheath can include an elongated base, and an elongated mandrel positioned above the elongated base. The elongated mandrel can include a conical end portion. The device for crimping an elongated sheath can also include a holding mechanism attached to the elongated base and supporting the elongated mandrel in an elevated position. The holding mechanism can include a first end piece including a crimping mechanism. The crimping mechanism can include a narrowing lumen that mates with the conical end portion of the mandrel. The device for crimping an elongated sheath can further include a second end piece that is movable relative to the elongated base such that a distance between the first end piece and the second end piece is adjustable.

In embodiments the conical end portion of the mandrel is positioned loosely within the narrowing lumen of the first end piece to facilitate passage of an elongated sheath over the conical end portion and through the narrowing lumen. In embodiments, the elongated base can include at least one elongated sliding track, the second end piece being slidably engaged with the at least one elongated sliding track via at least one reversible fastener. In embodiments, the reversible fastener can include a bolt extending through the second end piece, the elongated sliding track, and the elongated base. In embodiments, the mandrel can include a cylindrical end portion extending outwardly from the conical end portion, the cylindrical end portion defining an end of the mandrel.

In embodiments, the narrowing lumen of the crimping mechanism can include a first tapered portion opening toward the second end piece of the device, the first tapered portion having a narrow end that opens to a cylindrical portion of the narrowing lumen of the crimping mechanism. In embodiments, the narrowing lumen of the crimping mechanism can further include a second tapered portion opening away from the second end piece of the device and the first tapered portion, the second tapered portion having a narrow end that opens to the cylindrical portion of the narrowing lumen of the crimping mechanism.

In some embodiments, the second polymeric layer can extend longitudinally beyond the distal ends of the first polymeric layer, the braided layer, and the elastic layer to form a distal end portion of the sheath. The distal end portion can, in some embodiments, include multiple circumferential folds when the sheath is in a collapsed configuration. Furthermore, the distal end portion can, in some embodiments, include multiple layers of polymer material.

BRIEF DESCRIPTION OF THE DRAWINGS

FIG. 1 illustrates a delivery system for a cardiovascular prosthetic device, according to one embodiment.

FIG. 2 illustrates an expandable sheath that can be used in combination with the delivery system of FIG. 1, according to one embodiment.

FIG. 8 is a magnified view illustrating another embodiment of an expandable sheath.

FIG. 9 is a cross-sectional view of an apparatus that can be used to form an expandable sheath, according to one embodiment.

DETAILED DESCRIPTION

Figure 3:
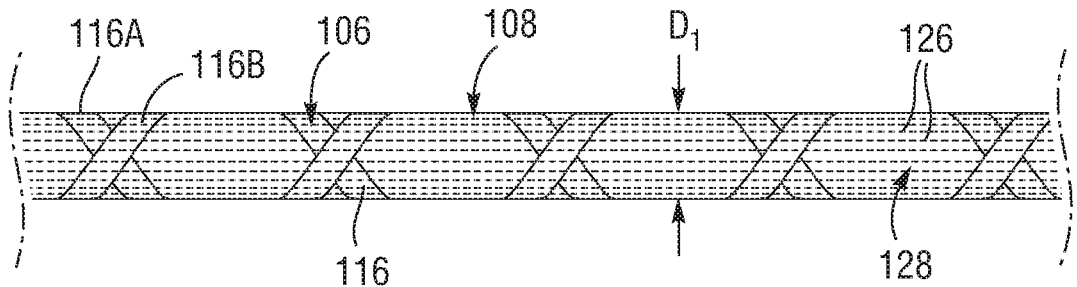
FIG. 3 is a magnified view of a portion of the expandable sheath of FIG. 2.

The expandable introducer sheaths described herein can be used to deliver a prosthetic device through a patient's vasculature to a procedure site within the body. The sheath can be constructed to be highly expandable and collapsible in the radial direction while limiting axial elongation of the sheath and, thereby, undesirable narrowing of the lumen. In one embodiment, the expandable sheath includes a braided layer, one or more relatively thin, non-elastic polymeric layers, and an elastic layer. The sheath can resiliently expand from its natural diameter to an expanded diameter as a prosthetic device is advanced through the sheath, and can return to its natural diameter upon passage of the prosthetic device under the influence of the elastic layer. In certain embodiments, the one or more polymeric layers can engage the braided layer, and can be configured to allow radial expansion of the braided layer while preventing axial elongation of the braided layer, which would otherwise result in elongation and narrowing of the sheath.

FIG. 1 illustrates a representative delivery apparatus 10 for delivering a medical device, such as a prosthetic heart valve or other prosthetic implant, to a patient. The delivery apparatus 10 is exemplary only, and can be used in combination with any of the expandable sheath embodiments described herein. Likewise, the sheaths disclosed herein can be used in combination with any of various known delivery apparatuses. The delivery apparatus 10 illustrated can generally include a steerable guide catheter 14 and a balloon catheter 16 extending through the guide catheter 14. A prosthetic device, such as a prosthetic heart valve 12, can be positioned on the distal end of the balloon catheter 16. The guide catheter 14 and the balloon catheter 16 can be adapted to slide longitudinally relative to each other to facilitate delivery and positioning of a prosthetic heart valve 12 at an implantation site in a patient's body. The guide catheter 14 includes a handle portion 18 and an elongated guide tube or shaft 20 extending from the handle portion 18.

The prosthetic heart valve 12 can be delivered into a patient's body in a radially compressed configuration and radially expanded to a radially expanded configuration at the desired deployment site. In the illustrated embodiment, the prosthetic heart valve 12 is a plastically expandable prosthetic valve that is delivered into the patient's body in a radially compressed configuration on a balloon of the balloon catheter 16 (as shown in FIG. 1) and then radially expanded to a radially expanded configuration at the deployment site by inflating the balloon (or by actuating another type of expansion device of the delivery apparatus). Further details regarding a plastically expandable heart valve that can be implanted using the devices disclosed herein are disclosed in U.S. Publication No. 2012/0123529, which is incorporated herein by reference. In other embodiments, the prosthetic heart valve 12 can be a self-expandable heart valve that is restrained in a radially compressed configuration by a sheath or other component of the delivery apparatus and self-expands to a radially expanded configuration when released by the sheath or other component of the delivery apparatus. Further details regarding a self-expandable heart valve that can be implanted using the devices disclosed herein are disclosed in U.S. Publication No. 2012/0239142, which is incorporated herein by reference. In still other embodiments, the prosthetic heart valve 12 can be a mechanically expandable heart valve that comprises a plurality of struts connected by hinges or pivot joints and is expandable from a radially compressed configuration to a radially expanded configuration by actuating an expansion mechanism that applies an expansion force to the prosthetic valve. Further details regarding a mechanically expandable heart valve that can be implanted using the devices disclosed herein are disclosed in U.S. Publication No. 2018/0153689, which is incorporated herein by reference. In still other embodiments, a prosthetic valve can incorporate two or more of the above-described technologies. For example, a self-expandable heart valve can be used in combination with an expansion device to assist expansion of the prosthetic heart valve.

Figure 4:
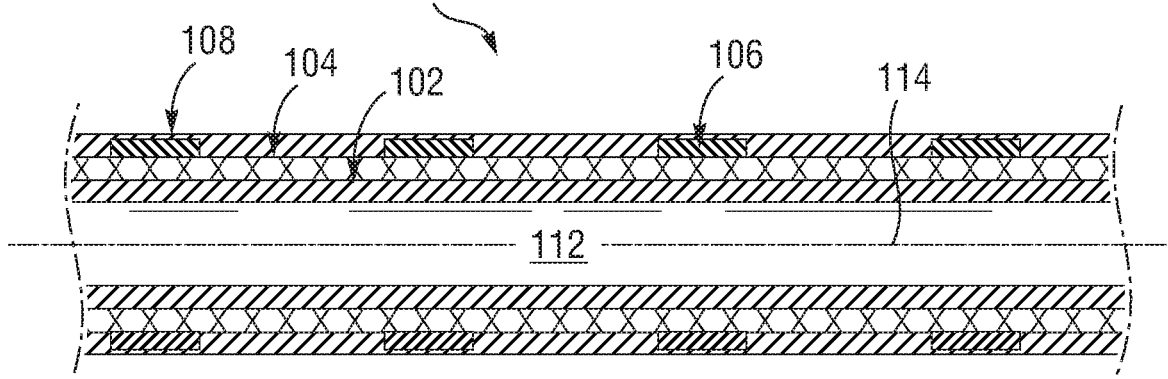
FIG. 4 is a side elevation cross-sectional view of a portion of the expandable sheath of FIG. 2.

FIG. 2 illustrates an assembly 90 (which can be referred to as an introducer device or assembly) that can be used to introduce the delivery apparatus 10 and the prosthetic device 12 into a patient's body, according to one embodiment. The introducer device 90 can comprise a housing 92 at a proximal end of the device and an expandable sheath 100 extending distally from the housing 92. The housing 92 can function as a handle for the device. The expandable sheath 100 has a central lumen 112 (FIG. 4) to guide passage of the delivery apparatus for the prosthetic heart valve. Generally, during use a distal end of the sheath 100 is passed through the skin of the patient and is inserted into a vessel, such as the femoral artery. The delivery apparatus 10 with its implant 12 can then be inserted through the housing 92 and the sheath 100, and advanced through the patient's vasculature to the treatment site, where the implant is to be delivered and implanted within the patient. In certain embodiments, the introducer housing 92 can include a hemostasis valve that forms a seal around the outer surface of the guide catheter 14 once inserted through the housing to prevent leakage of pressurized blood.

In alternative embodiments, the introducer device 90 need not include a housing 92. For example, the sheath 100 can be an integral part of a component of the delivery apparatus 10, such as the guide catheter. For example, the sheath can extend from the handle 18 of the guide catheter.

FIG. 3 illustrates the expandable sheath 100 in greater detail. With reference to FIG. 3, the sheath 100 can have a natural, unexpanded outer diameter $D_1$. In certain embodiments, the expandable sheath 100 can comprise a plurality of coaxial layers extending along at least a portion of the length L of the sheath (FIG. 2). For example, with reference to FIG. 4, the expandable sheath 100 can include a first layer 102 (also referred to as an inner layer), a second layer 104 disposed around and radially outward of the first layer 102, a third layer 106 disposed around and radially outward of the second layer 104, and a fourth layer 108 (also referred to as an outer layer) disposed around and radially outward of the third layer 106. In the illustrated configuration, the inner layer 102 can define the lumen 112 of the sheath extending along a central axis 114.

Referring to FIG. 3, when the sheath 100 is in an unexpanded state, the inner layer 102 and/or the outer layer 108 can form longitudinally-extending folds or creases such that the surface of the sheath comprises a plurality of ridges 126 (also referred to herein as "folds"). The ridges 126 can be circumferentially spaced apart from each other by longitudinally-extending valleys 128. When the sheath expands beyond its natural diameter $D_1$, the ridges 126 and the valleys 128 can level out or be taken up as the surface radially expands and the circumference increases, as further described below. When the sheath collapses back to its natural diameter, the ridges 126 and valleys 128 can reform.

In certain embodiments, the inner layer 102 and/or the outer layer 108 can comprise a relatively thin layer of polymeric material. For example, in some embodiments the thickness of the inner layer 102 can be from 0.01 mm to 0.5 mm, 0.02 mm to 0.4 mm, or 0.03 mm to 0.25 mm. In certain embodiments, the thickness of the outer layer 108 can be from 0.01 mm to 0.5 mm, 0.02 mm to 0.4 mm, or 0.03 mm to 0.25 mm.

In certain examples, the inner layer 102 and/or the outer layer 108 can comprise a lubricious, low-friction, and/or relatively non-elastic material. In particular embodiments, the inner layer 102 and/or the outer layer 108 can comprise a polymeric material having a modulus of elasticity of 400 MPa or greater. Exemplary materials can include ultra-high-molecular-weight polyethylene (UHMWPE) (e.g., Dyneema®), high-molecular-weight polyethylene (HMWPE), or polyether ether ketone (PEEK). With regard to the inner layer 102 in particular, such low coefficient of friction materials can facilitate passage of the prosthetic device through the lumen 112. Other suitable materials for the inner and outer layers can include polytetrafluoroethylene (PTFE), expanded polytetrafluoroethylene (ePTFE), ethylene tetrafluoroethylene (ETFE), nylon, polyethylene, polyether block amide (e.g., Pebax), and/or combinations of any of the above. Some embodiments of a sheath 100 can include a lubricious liner on the inner surface of the inner layer 102. Examples of suitable lubricious liners include materials that can further reduce the coefficient of friction of the inner layer 102, such as PTFE, polyethylene, polyvinylidine fluoride, and combinations thereof. Suitable materials for a lubricious liner also include other materials desirably having a coefficient of friction of 0.1 or less.

Additionally, some embodiments of the sheath 100 can include an exterior hydrophilic coating on the outer surface of the outer layer 108. Such a hydrophilic coating can facilitate insertion of the sheath 100 into a patient's vessel, reducing potential damage. Examples of suitable hydrophilic coatings include the Harmony™ Advanced Lubricity Coatings and other Advanced Hydrophilic Coatings available from SurModics, Inc., Eden Prairie, Minn. DSM medical coatings (available from Koninklijke DSM N.V, Heerlen, the Netherlands), as well as other hydrophilic coatings (e.g., PTFE, polyethylene, polyvinylidine fluoride), are also suitable for use with the sheath 100. Such hydrophilic coatings may also be included on the inner surface of the inner layer 102 to reduce friction between the sheath and the delivery system, thereby facilitating use and improving safety. In some embodiments, a hydrophobic coating, such as Perylene, may be used on the outer surface of the outer layer 108 or the inner surface of the inner layer 102 in order to reduce friction.

Figure 5A:
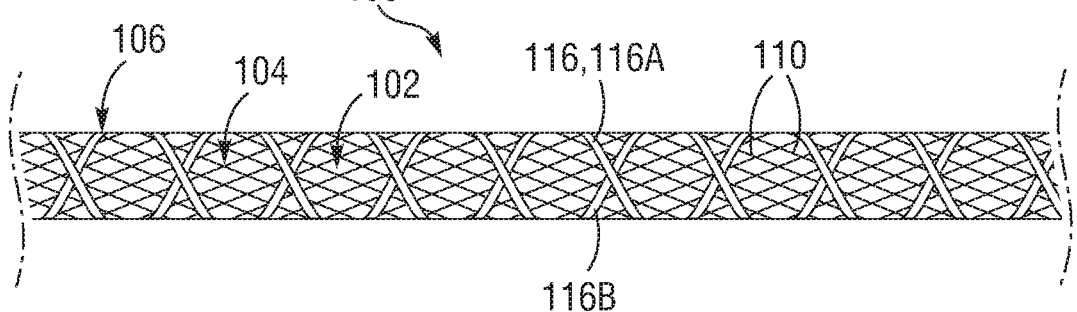
FIG. 5A is a magnified view of a portion of the expandable sheath of FIG. 2 with the outer layer removed for purposes of illustration.
Figure 5B:
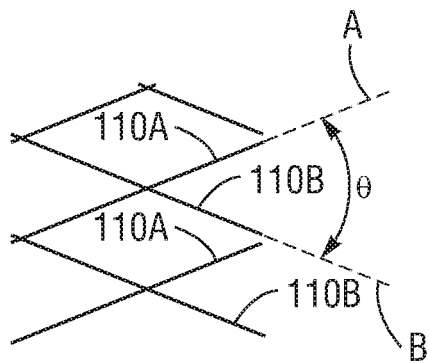
FIG. 5B is a magnified view of a portion of the braided layer of the sheath of FIG. 2.

In certain embodiments, the second layer 104 can be a braided layer. FIGS. 5A and 5B illustrate the sheath 100 with the outer layer 108 removed to expose the elastic layer 106. With reference to FIGS. 5A and 5B, the braided layer 104 can comprise a plurality of members or filaments 110 (e.g., metallic or synthetic wires or fibers) braided together. The braided layer 104 can have any desired number of filaments 110, which can be oriented and braided together along any suitable number of axes. For example, with reference to FIG. 5B, the filaments 110 can include a first set of filaments 110A oriented parallel to a first axis A, and a second set of filaments 110B oriented parallel to a second axis B. The filaments 110A and 110B can be braided together in a biaxial braid such that filaments 110A oriented along axis A form an angle $\theta$ with the filaments 110B oriented along axis B. In certain embodiments, the angle $\theta$ can be from 5° to 70°, 10° to 60°, 10° to 50°, or 10° to 45°. In the illustrated embodiment, the angle $\theta$ is 45°. In other embodiments, the filaments 110 can also be oriented along three axes and braided in a triaxial braid, or oriented along any number of axes and braided in any suitable braid pattern.

The braided layer 104 can extend along substantially the entire length L of the sheath 100, or alternatively, can extend only along a portion of the length of the sheath. In particular embodiments, the filaments 110 can be wires made from metal (e.g., Nitinol, stainless steel, etc.), or any of various polymers or polymer composite materials, such as carbon fiber. In certain embodiments, the filaments 110 can be round, and can have a diameter of from 0.01 mm to 0.5 mm, 0.03 mm to 0.4 mm, or 0.05 mm to 0.25 mm. In other embodiments, the filaments 110 can have a flat cross-section with dimensions of 0.01 mm×0.01 mm to 0.5 mm×0.5 mm, or 0.05 mm×0.05 mm to 0.25 mm×0.25 mm. In one embodiment, filaments 110 having a flat cross-section can have dimensions of 0.1 mm×0.2 mm. However, other geometries and sizes are also suitable for certain embodiments. If braided wire is used, the braid density can be varied. Some embodiments have a braid density of from ten picks per inch to eighty picks per inch, and can include eight wires, sixteen wires, or up to fifty-two wires in various braid patterns. In other embodiments, the second layer 104 can be laser cut from a tube, or laser-cut, stamped, punched, etc., from sheet stock and rolled into a tubular configuration. The layer 104 can also be woven or knitted, as desired.

The third layer 106 can be a resilient, elastic layer (also referred to as an elastic material layer). In certain embodiments, the elastic layer 106 can be configured to apply force to the underlying layers 102 and 104 in a radial direction (e.g., toward the central axis 114 of the sheath) when the sheath expands beyond its natural diameter by passage of the delivery apparatus through the sheath. Stated differently, the elastic layer 106 can be configured to apply encircling pressure to the layers of the sheath beneath the elastic layer 106 to counteract expansion of the sheath. The radially inwardly directed force is sufficient to cause the sheath to collapse radially back to its unexpanded state after the delivery apparatus is passed through the sheath.

In the illustrated embodiment, the elastic layer 106 can comprise one or more members configured as strands, ribbons, or bands 116 helically wrapped around the braided layer 104. For example, in the illustrated embodiment the elastic layer 106 comprises two elastic bands 116A and 116B wrapped around the braided layer with opposite helicity, although the elastic layer may comprise any number of bands depending upon the desired characteristics. The elastic bands 116A and 116B can be made from, for example, any of a variety of natural or synthetic elastomers, including silicone rubber, natural rubber, any of various thermoplastic elastomers, polyurethanes such as polyurethane siloxane copolymers, urethane, plasticized polyvinyl chloride (PVC), styrenic block copolymers, polyolefin elastomers, etc. In some embodiments, the elastic layer can comprise an elastomeric material having a modulus of elasticity of 200 MPa or less. In some embodiments, the elastic layer 106 can comprise a material exhibiting an elongation to break of 200% or greater, or an elongation to break of 400% or greater. The elastic layer 106 can also take other forms, such as a tubular layer comprising an elastomeric material, a mesh, a shrinkable polymer layer such as a heat-shrink tubing layer, etc. In lieu of, or in addition to, the elastic layer 106, the sheath 100 may also include an elastomeric or heat-shrink tubing layer around the outer layer 108. Examples of such elastomeric layers are disclosed in U.S. Publication No. 2014/0379067, U.S. Publication No. 2016/0296730, and U.S. Publication No. 2018/0008407, which are incorporated herein by reference. In other embodiments, the elastic layer 106 can also be radially outward of the polymeric layer 108.

In certain embodiments, one or both of the inner layer 102 and/or the outer layer 108 can be configured to resist axial elongation of the sheath 100 when the sheath expands. More particularly, one or both of the inner layer 102 and/or the outer layer 108 can resist stretching against longitudinal forces caused by friction between a prosthetic device and the inner surface of the sheath such that the length L remains substantially constant as the sheath expands and contracts. As used herein with reference to the length L of the sheath, the term "substantially constant" means that the length L of the sheath increases by not more than 1%, by not more than 5%, by not more than 10%, by not more than 15%, or by not more than 20%. Meanwhile, with reference to FIG. 5B, the filaments 110A and 110B of the braided layer can be allowed to move angularly relative to each other such that the angle θ changes as the sheath expands and contracts. This, in combination with the longitudinal folds 126 in the layers 102 and 108, can allow the lumen 112 of the sheath to expand as a prosthetic device is advanced through it.

For example, in some embodiments the inner layer 102 and the outer layer 108 can be heat-bonded during the manufacturing process such that the braided layer 104 and the elastic layer 106 are encapsulated between the layers 102 and 108. More specifically, in certain embodiments the inner layer 102 and the outer layer 108 can be adhered to each other through the spaces between the filaments 110 of the braided layer 104 and/or the spaces between the elastic bands 116. The layers 102 and 108 can also be bonded or adhered together at the proximal and/or distal ends of the sheath. In certain embodiments, the layers 102 and 108 are not adhered to the filaments 110. This can allow the filaments 110 to move angularly relative to each other, and relative to the layers 102 and 108, allowing the diameter of the braided layer 104, and thereby the diameter of the sheath, to increase or decrease. As the angle θ between the filaments 110A and 110B changes, the length of the braided layer 104 can also change. For example, as the angle θ increases, the braided layer 104 can foreshorten, and as the angle θ decreases, the braided layer 104 can lengthen to the extent permitted by the areas where the layers 102 and 108 are bonded. However, because the braided layer 104 is not adhered to the layers 102 and 108, the change in length of the braided layer that accompanies a change in the angle θ between the filaments 110A and 110B does not result in a significant change in the length L of the sheath.

Figure 6:
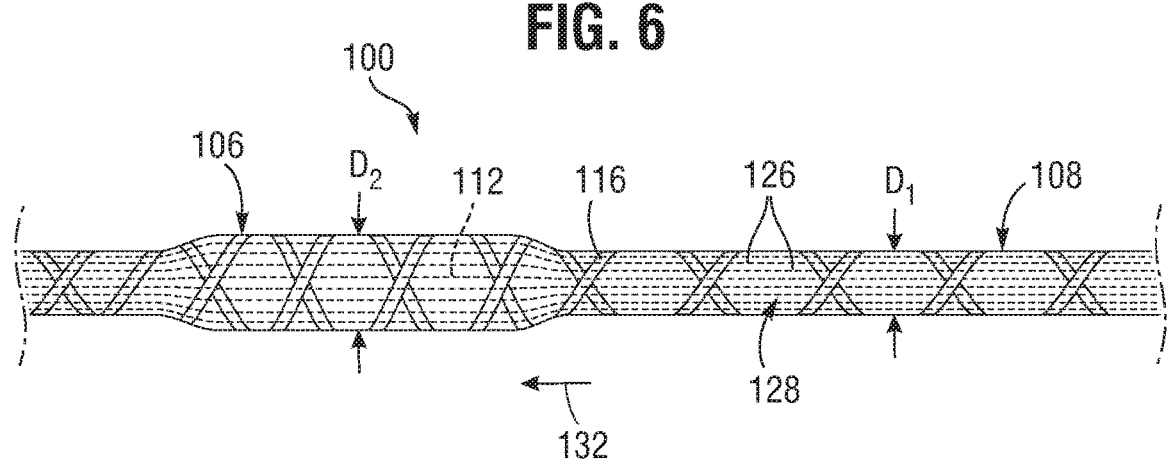
FIG. 6 is a magnified view of a portion of the expandable sheath of FIG. 2 illustrating expansion of the sheath as a prosthetic device is advanced through the sheath.

FIG. 6 illustrates radial expansion of the sheath 100 as a prosthetic device 12 is passed through the sheath in the direction of arrow 132 (e.g., distally). As the prosthetic device 12 is advanced through the sheath 100, the sheath can resiliently expand to a second diameter $D_2$ that corresponds to a size or diameter of the prosthetic device. As the prosthetic device 12 is advanced through the sheath 100, the prosthetic device can apply longitudinal force to the sheath in the direction of motion by virtue of the frictional contact between the prosthetic device and the inner surface of the sheath. However, as noted above, the inner layer 102 and/or the outer layer 108 can resist axial elongation such that the length L of the sheath remains constant, or substantially constant. This can reduce or prevent the braided layer 104 from lengthening, and thereby constricting the lumen 112.

Meanwhile, the angle θ between the filaments 110A and 110B can increase as the sheath expands to the second diameter $D_2$ to accommodate the prosthetic valve. This can cause the braided layer 104 to foreshorten. However, because the filaments 110 are not engaged or adhered to the layers 102 or 108, the shortening of the braided layer 104 attendant to an increase in the angle θ does not affect the overall length L of the sheath. Moreover, because of the longitudinally-extending folds 126 formed in the layers 102 and 108, the layers 102 and 108 can expand to the second diameter $D_2$ without rupturing, in spite of being relatively thin and relatively non-elastic. In this manner, the sheath 100 can resiliently expand from its natural diameter $D_1$ to a second diameter $D_2$ that is larger than the diameter $D_1$ as a prosthetic device is advanced through the sheath, without lengthening, and without constricting. Thus, the force required to push the prosthetic implant through the sheath is significantly reduced.

Additionally, because of the radial force applied by the elastic layer 106, the radial expansion of the sheath 100 can be localized to the specific portion of the sheath occupied by the prosthetic device. For example, with reference to FIG. 6, as the prosthetic device 12 moves distally through the sheath 100, the portion of the sheath immediately proximal to the prosthetic device 12 can radially collapse back to the initial diameter $D_1$ under the influence of the elastic layer 106. The layers 102 and 108 can also buckle as the circumference of the sheath is reduced, causing the ridges 126 and the valleys 128 to reform. This can reduce the size of the sheath required to introduce a prosthetic device of a given size. Additionally, the temporary, localized nature of the expansion can reduce trauma to the blood vessel into which the sheath is inserted, along with the surrounding tissue, because only the portion of the sheath occupied by the prosthetic device expands beyond the sheath's natural diameter and the sheath collapses back to the initial diameter once the device has passed. This limits the amount of tissue that must be stretched in order to introduce the prosthetic device, and the amount of time for which a given portion of the vessel must be dilated.

In addition to the advantages above, the expandable sheath embodiments described herein can provide surprisingly superior performance relative to known introducer sheaths. For example, it is possible to use a sheath configured as described herein to deliver a prosthetic device having a diameter that is two times larger, 2.5 times larger, or even three times larger than the natural outer diameter of the sheath. For example, in one embodiment a crimped prosthetic heart valve having a diameter of 7.2 mm was successfully advanced through a sheath configured as described above and having a natural outer diameter of 3.7 mm. As the prosthetic valve was advanced through the sheath, the outer diameter of the portion of the sheath occupied by the prosthetic valve increased to 8 mm. In other words, it was possible to advance a prosthetic device having a diameter more than two times the outer diameter of the sheath through the sheath, during which the outer diameter of the sheath resiliently increased by 216%. In another example, a sheath with an initial or natural outer diameter of 4.5 mm to 5 mm can be configured to expand to an outer diameter of 8 mm to 9 mm.

In alternative embodiments, the sheath 100 may optionally include the layer 102 without the layer 108, or the layer 108 without the layer 102, depending upon the particular characteristics desired.

Figure 10A:
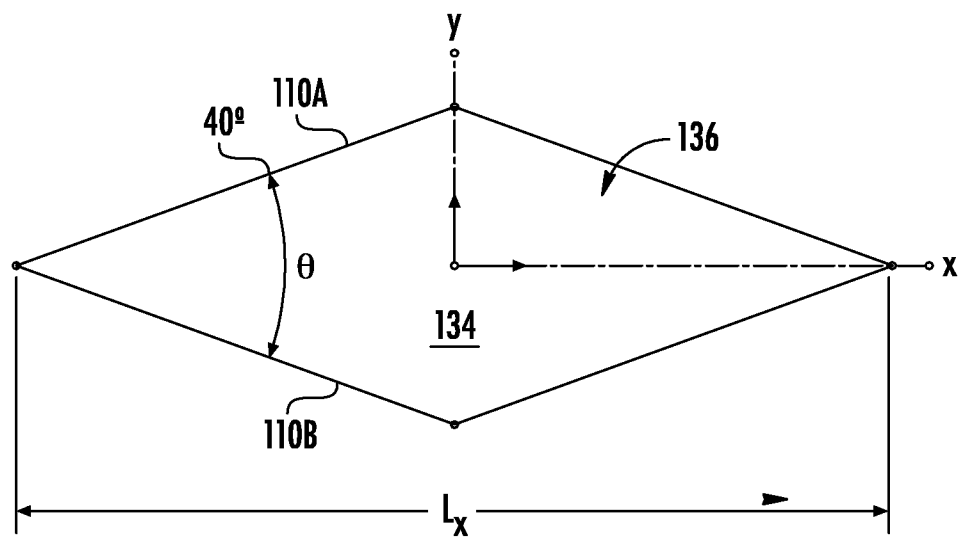
FIGS. 10A-10D illustrate another embodiment of a braided layer in which the filaments of the braided layer are configured to buckle when the sheath is in a radially collapsed state.
Figure 10B:
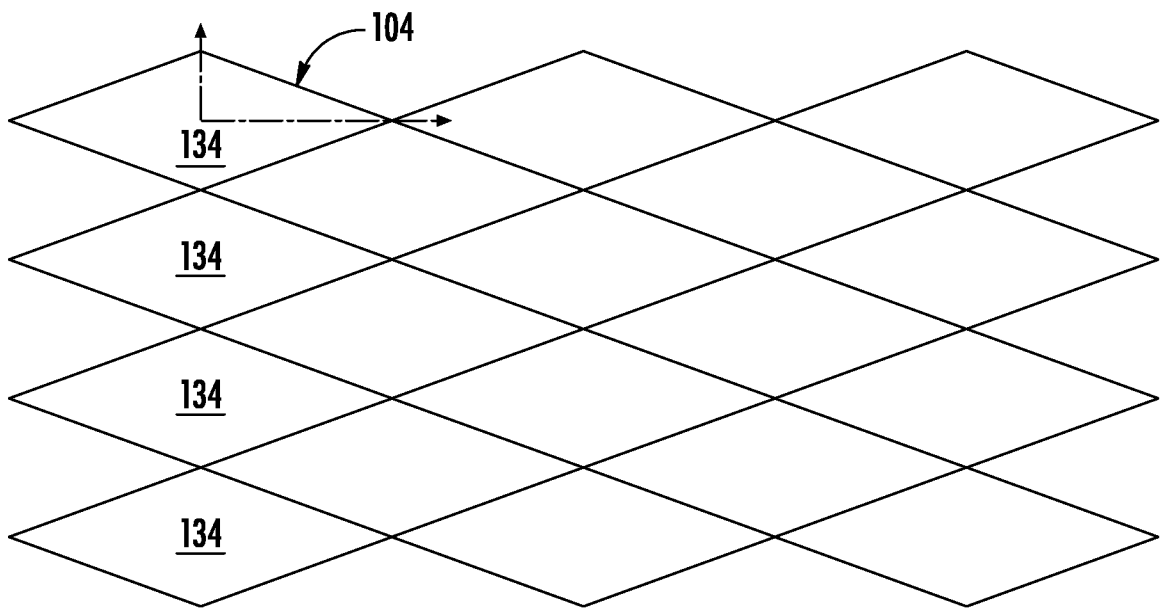

FIGS. 10A-10D illustrate another embodiment of the braided layer 104 in which the filaments 110 are configured to buckle. For example, FIG. 10A illustrates a unit cell 134 of the braided layer 104 in a configuration corresponding to the braided layer in a fully expanded state. For example, the expanded state illustrated in FIG. 10A can correspond to the diameter $D_2$ described above, and/or a diameter of the braided layer during initial construction of the sheath 100 before the sheath is radially collapsed to its functional design diameter $D_1$, as described further below with reference to FIG. 7. The angle θ between the filaments 110A and 110B can be, for example, 40°, and the unit cell 134 can have a length $L_x$ along the x-direction (note Cartesian coordinate axes shown). FIG. 10B illustrates a portion of the braided layer 104 including an array of unit cells 134 in the expanded state.

Figure 10C:
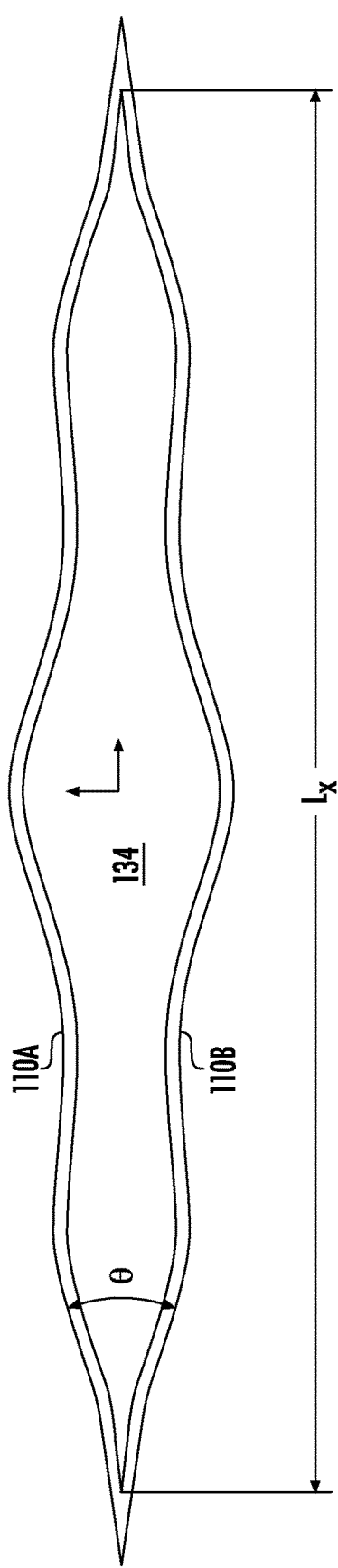
Figure 10D:
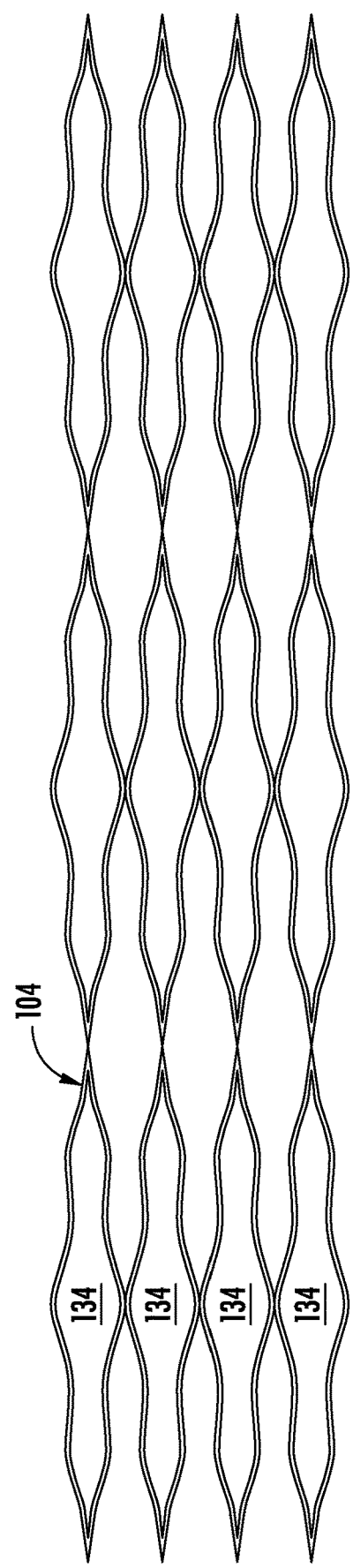

In the illustrated embodiments, the braided layer 104 is disposed between the polymeric layers 102 and 108, as described above. For example, the polymeric layers 102 and 108 can be adhered or laminated to each other at the ends of the sheath 100 and/or between the filaments 110 in the open spaces 136 defined by the unit cells 134. Thus, with reference to FIGS. 10C and 10D, when the sheath 100 is radially collapsed to its functional diameter $D_1$, the diameter of the braided layer 104 can decrease as the angle θ decreases. However, the bonded polymeric layers 102 and 108 can constrain or prevent the braided layer 104 from lengthening as it radially collapses. This can cause the filaments 110 to resiliently buckle in the axial direction, as shown in FIGS. 10C and 10D. The degree of buckling can be such that the length $L_x$ of the unit cells 134 is the same, or substantially the same, between the collapsed and fully expanded diameters of the sheath. This means that the overall length of the braided layer 104 can remain constant, or substantially constant, between the natural diameter $D_1$ of the sheath and the expanded diameter Dz. As the sheath expands from in its initial diameter $D_1$ during passage of a medical device, the filaments 110 can straighten as the buckling is relieved, and the sheath can radially expand. As the medical device passes through the sheath, the braided layer 104 can be urged back to the initial diameter $D_1$ by the elastic layer 106, and the filaments 110 can resiliently buckle again. Using the configuration of FIGS. 10A-10C, it is also possible to accommodate a prosthetic device having a diameter that is two times larger, 2.5 times larger, or even three times larger than the natural outer diameter $D_1$ of the sheath.

Figure 7:
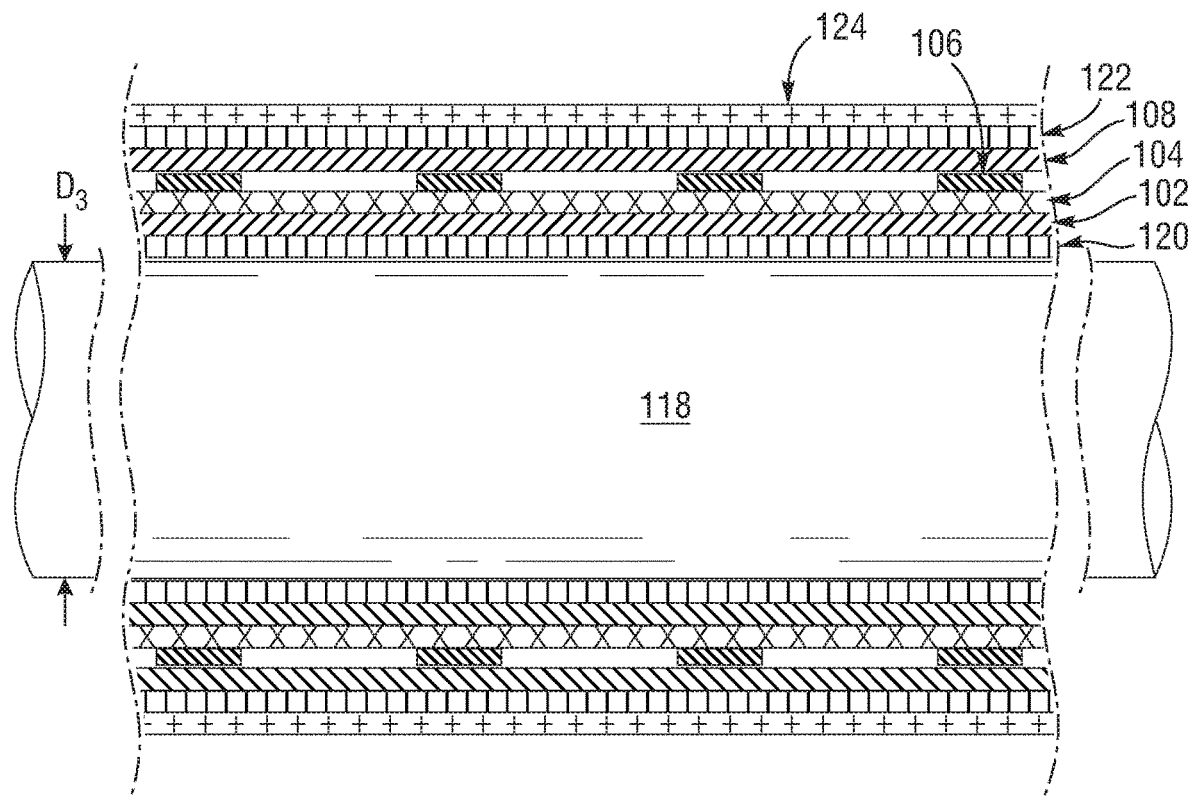
FIG. 7 is a magnified, partial cross-sectional view illustrating the constituent layers of the sheath of FIG. 2 disposed on a mandrel.

Turning now to methods of making expandable sheaths, FIG. 7 illustrates the layers 102-108 of the expandable sheath 100 disposed on a cylindrical mandrel 118, according to one embodiment. In certain embodiments, the mandrel 118 can have a diameter $D_3$ that is greater than the desired natural outer diameter $D_1$ of the finished sheath. For example, in some embodiments a ratio of the diameter $D_3$ of the mandrel to the outer diameter $D_1$ of the sheath can be 1.5:1, 2:1, 2.5:1, 3:1, or greater. In certain embodiments, the diameter $D_3$ of the mandrel can be equal to the expanded diameter $D_2$ of the sheath. In other words, the diameter $D_3$ of the mandrel can be the same, or nearly the same, as the desired expanded diameter $D_2$ of the sheath when a prosthetic device is being advanced through the sheath. Thus, in certain embodiments a ratio of the expanded outer diameter $D_2$ of the expanded sheath to the collapsed outer diameter $D_1$ of the unexpanded sheath can be 1.5:1, 2:1, 2.5:1, 3:1, or greater.

With reference to FIG. 7, the expandable sheath 100 can be made by wrapping or situating an ePTFE layer 120 around the mandrel 118, followed by the first polymeric layer 102. In some embodiments, the ePTFE layer can aid in removing the sheath 100 from the mandrel 118 upon completion of the fabrication process. The first polymeric layer 102 may be in the form of a pre-fabricated sheet that is applied by being wrapped around the mandrel 118, or may be applied to the mandrel by dip-coating, electro-spinning, etc. The braided layer 104 can be situated around the first layer 102, followed by the elastic layer 106. In embodiments in which the elastic layer 106 comprises one or more elastic bands 116, the bands 116 can be helically wrapped around the braided layer 104. In other embodiments, the elastic layer 106 may be dip-coated, electro-spun, etc. The outer polymeric layer 108 can then be wrapped, situated, or applied around the elastic layer 106, followed by another layer 122 of ePTFE and one or more layers 124 of heat-shrink tubing or heat-shrink tape.

In particular embodiments, the elastic bands 116 can be applied to the braided layer 104 in a stretched, taut, or extended condition. For example, in certain embodiments the bands 116 can be applied to the braided layer 104 stretched to a length that is twice their natural, relaxed length. This will cause the completed sheath to radially collapse under the influence of the elastic layer when removed from the mandrel, which can cause corresponding relaxation of the elastic layer, as described below. In other embodiments, the layer 102 and the braided layer 104 can be removed from the mandrel, the elastic layer 106 can be applied in a relaxed state or moderately stretched state, and then the assembly can be placed back on the mandrel such that the elastic layer is radially expanded and stretched to a taut condition prior to application of the outer layer 108.

The assembly can then be heated to a sufficiently high temperature that the heat-shrink layer 124 shrinks and compresses the layers 102-108 together. In certain embodiments, the assembly can be heated to a sufficiently high temperature such that the polymeric inner and outer layers 102 and 108 become soft and tacky, and bond to each other in the open spaces between the braided layer 104 and the elastic layer 106 and encapsulate the braided layer and the elastic layer. In other embodiments, the inner and outer layers 102, 108 can be reflowed or melted such that they flow around and through the braided layer 104 and the elastic layer 106. In an exemplary embodiment, the assembly can be heated at 150° C. for 20-30 minutes.

After heating, the sheath 100 can be removed from the mandrel 118, and the heat-shrink tubing 124 and the ePTFE layers 120 and 122 can be removed. Upon being removed from the mandrel 118, the sheath 100 can at least partially radially collapse to the natural design diameter $D_1$ under the influence of the elastic layer 106. In certain embodiments, the sheath can be radially collapsed to the design diameter with the optional aid of a crimping mechanism. The attendant reduction in circumference can buckle the filaments 110 as shown in FIGS. 10C and 10D, along with the inner and outer layers 102 and 108 to form the longitudinally-extending folds 126.

In certain embodiments, a layer of PTFE can be interposed between the ePTFE layer 120 and the inner layer 102, and/or between the outer layer 108 and the ePTFE layer 122, in order to facilitate separation of the inner and outer polymeric layers 102, 108 from the respective ePTFE layers 120 and 122. In further embodiments, one of the inner layer 102 or the outer layer 108 may be omitted, as described above.

FIG. 8 illustrates another embodiment of the expandable sheath 100 including one or more members configured as yarns or cords 130 extending longitudinally along the sheath and attached to the braided layer 104. Although only one cord 130 is illustrated in FIG. 8, in practice the sheath may include two cords, four cords, six cords, etc., arrayed around the circumference of the sheath at equal angular spacings. The cords 130 can be sutured to the exterior of the braided layer 104, although other configurations and attachment methods are possible. By virtue of being attached to the braided layer 104, the cords 130 can be configured to prevent axial elongation of the braided layer 104 when a prosthetic device is passed through the sheath. The cords 130 may be employed in combination with the elastic layer 106, or separately. The cords 130 may also be used in combination with one or both of the inner and/or outer layers 102 and 108, depending upon the particular characteristics desired. The cords 130 may also be disposed on the inside of the braided layer 104 (e.g., between the inner layer 102 and the braided layer 104).

The expandable sheath 100 can also be made in other ways. For example, FIG. 9 illustrates an apparatus 200 including a containment vessel 202 and a heating system schematically illustrated at 214. The apparatus 200 is particularly suited for forming devices (medical devices or devices for non-medical uses) comprised of two or more layers of material. Devices formed by the apparatus 200 can be formed from two or more co-axial layers of material, such as the sheath 100, or shafts for catheters. Devices formed by the apparatus 200 alternatively can be formed by two or more non-coaxial layers, such as two or more layers stacked on top of each other.

The containment vessel 202 can define an interior volume or chamber 204. In the illustrated embodiment, the vessel 202 can be a metal tube including a closed end 206 and an open end 208. The vessel 202 can be at least partially filled with a thermally-expandable material 210 having a relatively high coefficient of thermal expansion. In particular embodiments, the thermally-expandable material 210 may have a coefficient of thermal expansion of $2.4 \times 10^{-4}$/° C. or greater. Exemplary thermally-expandable materials include elastomers such as silicones materials. Silicone materials can have a coefficient of thermal expansion of from $5.9 \times 10^{-4}$/° C. to $7.9 \times 10^{-4}$/° C.

A mandrel similar to the mandrel 118 of FIG. 7 and including the desired combination of sheath material layers disposed around it can be inserted into the thermally-expandable material 210. Alternatively, the mandrel 118 can be inserted into the chamber 204, and the remaining volume of the chamber can be filled with the thermally-expandable material 210 so that the mandrel is surrounded by the material 210. The mandrel 118 is shown schematically for purposes of illustration. As such, the mandrel 118 can be cylindrical as depicted in FIG. 7. Likewise, the inner surface of the material 210 and the inner surface of the vessel 202 can have a cylindrical shape that corresponds to the shape of the mandrel 118 and the final shape of the sheath 100. To facilitate placement of a cylindrical or rounded mandrel 118, the vessel 202 can comprise two portions that are connected to each other by a hinge to allow the two portions to move between an open configuration for placing the mandrel inside of the vessel and a closed configuration extending around the mandrel. For example, the upper and lower halves of the vessel shown in FIG. 9 can be connected to each other by a hinge at the closed side of the vessel (the left side of the vessel in FIG. 9).

The open end 208 of the vessel 202 can be closed with a cap 212. The vessel 202 can then be heated by the heating system 214. Heating by the heating system 214 can cause the material 210 to expand within the chamber 204 and apply radial pressure against the layers of material on the mandrel 118. The combination of the heat and pressure can cause the layers on the mandrel 118 to bond or adhere to each other to form a sheath. In certain embodiments, it is possible to apply radial pressure of 100 MPa or more to the mandrel 118 using the apparatus 200. The amount of radial force applied to the mandrel can be controlled by, for example, the type and quantity of the material 210 selected and its coefficient of thermal expansion, the thickness of the material 210 surrounding the mandrel 118, the temperature to which the material 210 is heated, etc.

In some embodiments, the heating system 214 can be an oven into which the vessel 202 is placed. In some embodiments, the heating system can include one or more heating elements positioned around the vessel 202. In some embodiments, the vessel 202 can be an electrical resistance heating element or an induction heating element controlled by the heating system 214. In some embodiments, heating elements can be embedded in the thermally-expandable material 210. In some embodiments, the material 210 can be configured as a heating element by, for example, adding electrically conductive filler materials, such as carbon fibers or metal particles.

The apparatus 200 can provide several advantages over known methods of sheath fabrication, including uniform, highly controllable application of radial force to the mandrel 118 along its length, and high repeatability. The apparatus 200 can also facilitate fast and accurate heating of the thermally-expandable material 210, and can reduce or eliminate the need for heat-shrink tubing and/or tape, reducing material costs and labor. The amount of radial force applied can also be varied along the length of the mandrel by, for example, varying the type or thickness of the surrounding material 210. In certain embodiments, multiple vessels 202 can be processed in a single fixture, and/or multiple sheaths can be processed within a single vessel 202. The apparatus 200 can also be used to produce other devices, such as shafts or catheters.

In one specific method, the sheath 100 can be formed by placing layers 102, 104, 106, 108 on the mandrel 118 and placing the mandrel with the layers inside of the vessel 202 with the thermally-expandable material 210 surrounding the outermost layer 108. If desired, one or more inner layers 120 of ePTFE (or similar material) and one or more outer layers 122 of ePTFE (or similar material) can be used (as shown in FIG. 7) to facilitate removal of the finished sheath from the mandrel 118 and the material 210. The assembly is then heated with the heating system 214 to reflow the layers 102, 108. Upon subsequent cooling, the layers 102, 108 become at least partially bonded to each other and at least partially encapsulate layers 104, 106.

Figure 11:
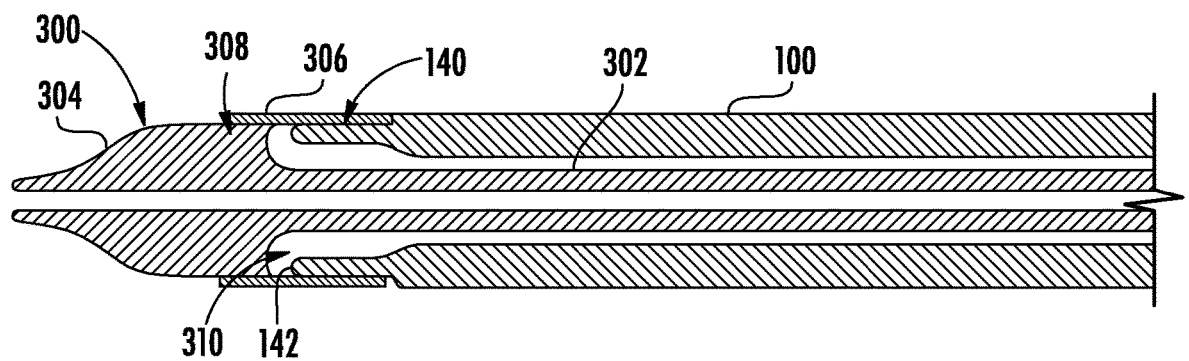
FIG. 11 shows a side cross-sectional view of an assembly of an expandable sheath with a vessel dilator.
Figure 12:
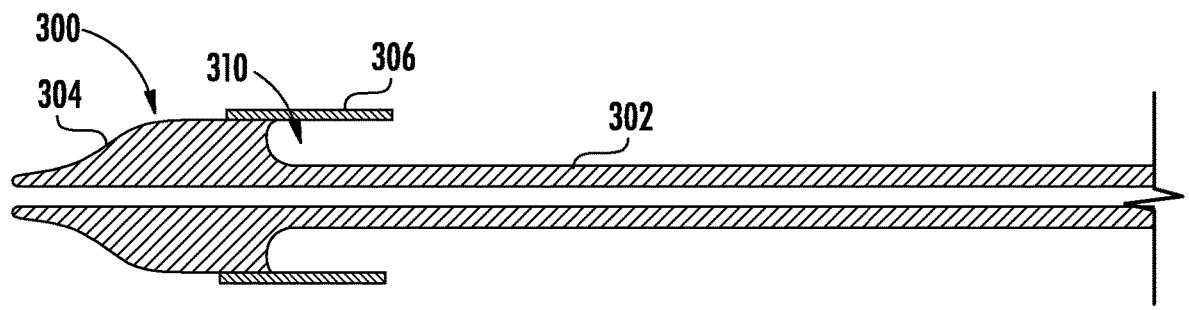
FIG. 12 shows the vessel dilator of the assembly embodiment of FIG. 11.

FIG. 11 illustrates another embodiment in which the expandable sheath 100 is configured to receive an apparatus configured as a pre-introducer or vessel dilator 300. In particular embodiments, the introducer device 90 can include the vessel dilator 300. Referring to FIG. 12, the vessel dilator 300 can comprise a shaft member 302 including a tapered dilator member configured as a nose cone 304 located at the distal end portion of the shaft member 302. The vessel dilator 300 can further comprise a capsule or retaining member 306 extending proximally from a proximal end portion 308 of the nose cone 304 such that a circumferential space 310 is defined between the exterior surface of the shaft member 302 and the interior surface of the retaining member 306. In certain embodiments, the retaining member 306 can be configured as a thin polymeric layer or sheet, as further described below.

Figure 13:
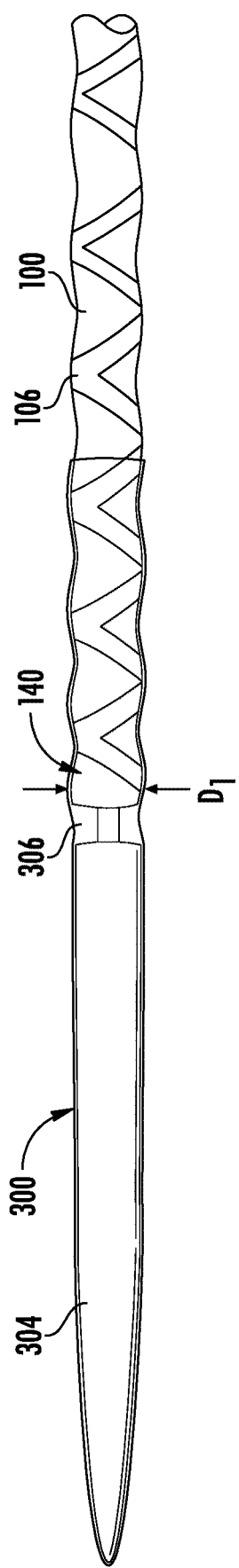
FIG. 13 shows a side view of another assembly embodiment including an expandable sheath and a vessel dilator.
Figure 14:
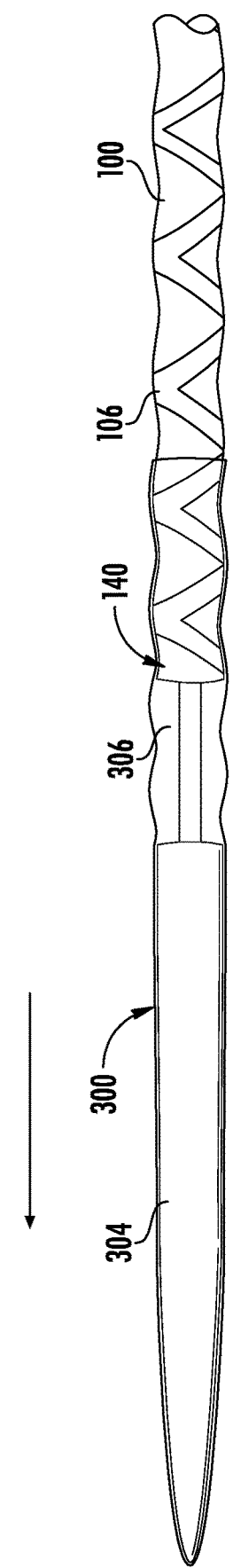
FIG. 14 shows a side view of the assembly embodiment of FIG. 13, with the vessel dilator pushed partially away from the expandable sheath.

Referring to FIGS. 11 and 13, a first or distal end portion 140 of the sheath 100 can be received in the space 310 such that the sheath engages the nose cone 304, and/or such that the retaining member 306 extends over the distal end portion 140 of the sheath. In use, the coupled or assembled vessel dilator 300 and sheath 100 can then be inserted through an incision into a blood vessel. The tapered cone shape of the nose cone 304 can aid in gradually dilating the blood vessel and access site while minimizing trauma to the blood vessel and surrounding tissue. Once the assembly has been inserted to the desired depth, the vessel dilator 300 can be advanced further into the blood vessel (e.g., distally) while the sheath 100 is held steady, as illustrated in FIG. 14.

Figure 15:
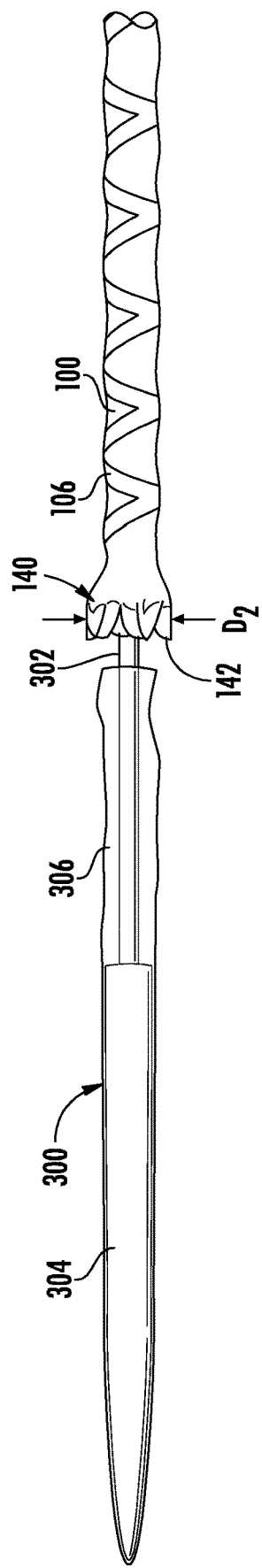
FIG. 15 shows a side view of the assembly embodiment of FIG. 13, with the vessel dilator pushed fully away from the expandable sheath.
Figure 16:
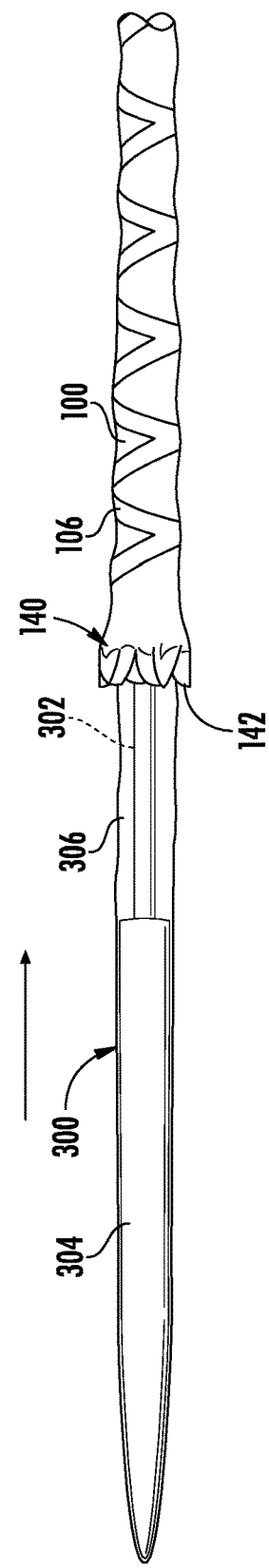
FIG. 16 shows a side view of the assembly embodiment of FIG. 13, with the vessel dilator being retracted into the expandable sheath.
Figure 17:
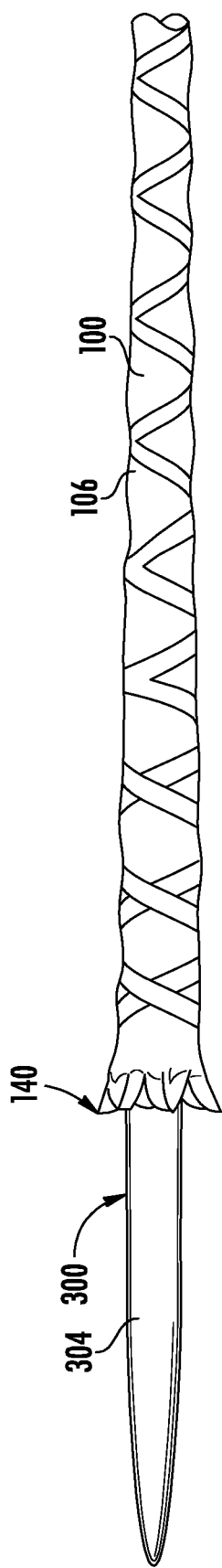
FIG. 17 shows a side view of the assembly embodiment of FIG. 13, with the vessel dilator being retracted further into the expandable sheath.
Figure 18:
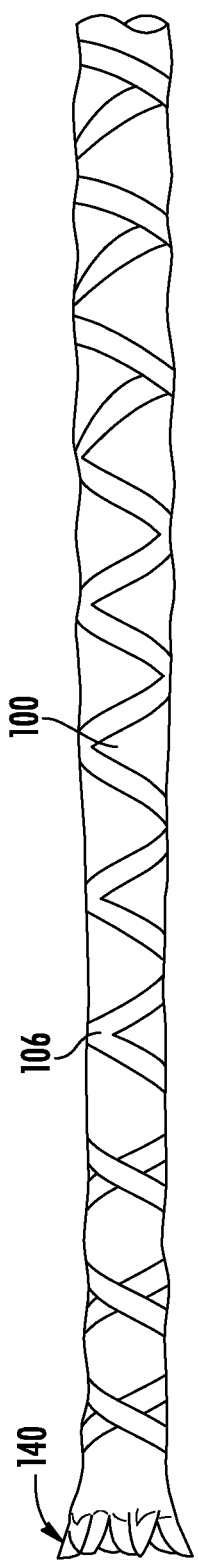
FIG. 18 shows a side view of the assembly embodiment of FIG. 13, with the vessel dilator being fully retracted into the expandable sheath.

Referring to FIG. 15, the vessel dilator 300 can be advanced distally through the sheath 100 until the retaining member 306 is removed from over the distal end portion 140 of the sheath 100. In certain embodiments, the helically-wrapped elastic layer 106 of the sheath can terminate proximally of the distal end 142 of the sheath. Thus, when the distal end portion 140 of the sheath is uncovered, the distal end portion (which can be heat-set) can flare or expand, increasing the diameter of the opening at the distal end 142 from the first diameter $D_1$ (FIG. 13) to a second, larger diameter $D_2$ (FIG. 15). The vessel dilator 300 can then be withdrawn through the sheath 100 as illustrated in FIGS. 16-18, leaving the sheath 100 in place in the vessel.

The vessel dilator 300 can include a variety of active and/or passive mechanisms for engaging and retaining the sheath 100. For example, in certain embodiments the retaining member 306 can comprise a polymeric heat-shrink layer that can be collapsed around the distal end portion of the sheath 100. In the embodiment illustrated in FIG. 1, the retaining member can comprise an elastic member configured to compress the distal end portion 140 of the sheath 100. In yet other embodiments, the retaining member 306 and the sheath 100 can be glued or fused (e.g., heat-bonded) together in a manner such that application of selected amount of force can break the adhesive bonds between retaining member 306 free from the sheath 100 to allow the vessel dilator to be withdrawn. In some embodiments, the end portion of the braided layer 104 can be heat set to flare or expand radially inwardly or outwardly, in order to apply pressure to a corresponding portion of the vessel dilator 300.

Figure 19:
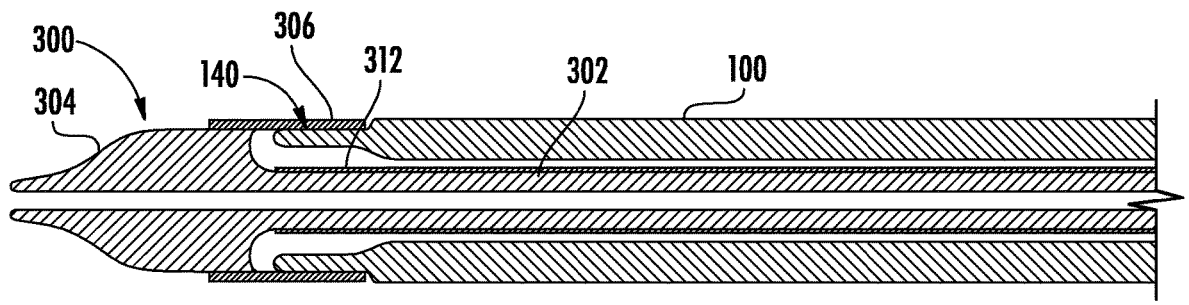
FIG. 19 shows a side cross sectional view of another assembly embodiment including an expandable sheath and a vessel dilator.

Referring to FIG. 19, the assembly can include a mechanically-actuated retaining mechanism, such as a shaft 312 disposed between the dilator shaft member 302 and the sheath 100. In certain embodiments, the shaft 312 can releasably couple the vessel dilator 300 to the sheath 100, and can be actuated from outside the body (i.e., manually deactivated).

Figure 20:
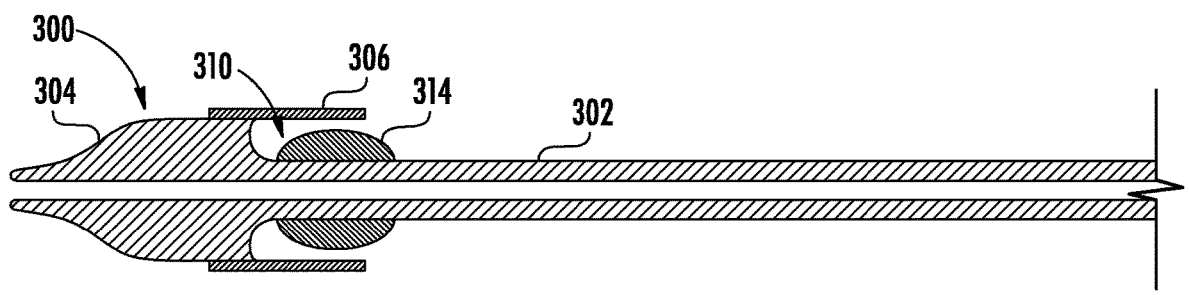
FIG. 20 illustrates and embodiment of a vessel dilator that may be used in combination with the expandable sheaths described herein.
Figure 21:
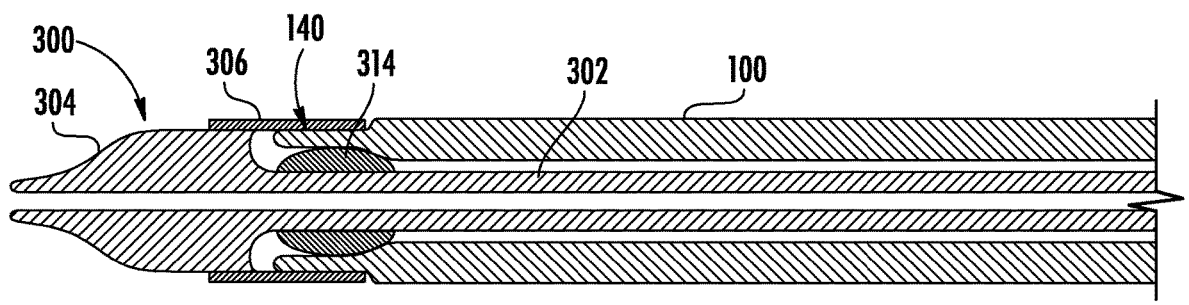
FIG. 21 illustrates an embodiment of a vessel dilator that may be used in combination with the expandable sheaths described herein.

Referring to FIGS. 20 and 21, in some embodiments the shaft 304 can comprise one or more balloons 314 arrayed circumferentially around its exterior surface and configured to engage the sheath 100 when inflated. The balloons 314 can be selectively deflated in order to release the sheath 100 and withdraw the vessel dilator. For example, when inflated, the balloons press the captured distal end portion of the sheath 100 against the inner surface of the capsule 306 to assist in retaining the sheath in place relative to the vessel dilator. When the balloons are deflated, the vessel dilator can be more easily moved relative to the sheath 100.

Figure 22:
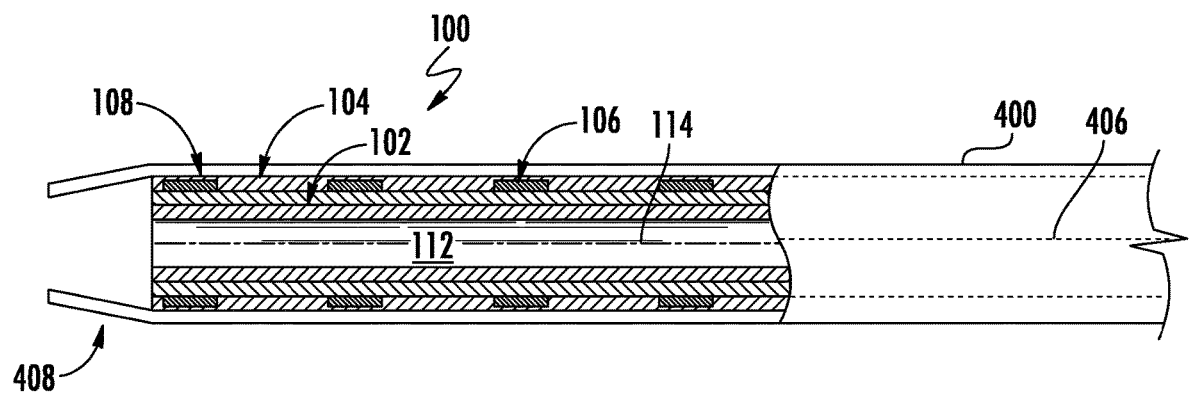
FIG. 22 shows a side view with a cutaway to cross section of an embodiment of an expandable sheath having an outer cover and an overhang.

In another embodiment, an expandable sheath configured as described above can further comprise a shrinkable polymeric outer cover, such as a heat-shrink tubing layer 400 shown in FIG. 22. The heat-shrink tubing layer 400 can be configured to allow a smooth transition between the vessel dilator 300 and the distal end portion 140 of the sheath. The heat-shrink tubing layer 400 can also constrain the sheath to a selected initial, reduced outer diameter. In certain embodiments, the heat-shrink tubing layer 400 extends fully over the length of the sheath 100 and can be attached to the sheath handle by a mechanical fixation means, such as a clamp, nut, adhesive, heat welding, laser welding, or an elastic clamp. In some embodiments, the sheath is press-fit into the heat-shrink tubing layer during manufacturing.

In some embodiments, the heat-shrink tubing layer 400 can extend distally beyond the distal end portion 140 of the sheath as the distal overhang 408 shown in FIG. 22. A vessel dilator can be inserted through the sheath lumen 112 and beyond the distal edge of the overhang 408. The overhang 408 conforms tightly to the inserted vessel dilator to give a smooth transition between the dilator diameter and the sheath diameter to ease insertion of the combined dilator and sheath. When the vessel dilator is removed, overhang 408 remains in the vessel as part of sheath 100. The heat shrink tubing layer 400 offers the additional benefit of shrinking the overall outer diameter of the sheath along the longitudinal axis.

In some embodiments, the heat-shrink tubing layer can be configured to split open as a delivery apparatus such as the delivery apparatus 10 is advanced through the sheath. For example, in certain embodiments, the heat-shrink tubing layer can comprise one or more longitudinally extending openings, slits, or weakened, elongated scorelines 406 such as those shown in FIG. 22 configured to initiate splitting of the layer at a selected location. As the delivery apparatus 10 is advanced through the sheath, the heat-shrink tubing layer 400 can continue to split open, allowing the sheath to expand as described above with reduced force. In certain embodiments, the sheath need not comprise the elastic layer 106 such that the sheath automatically expands from the initial, reduce diameter when the heat-shrink tubing layer splits open. The heat shrink tubing layer 400 can comprise polyethylene or other suitable materials.

Figure 23:
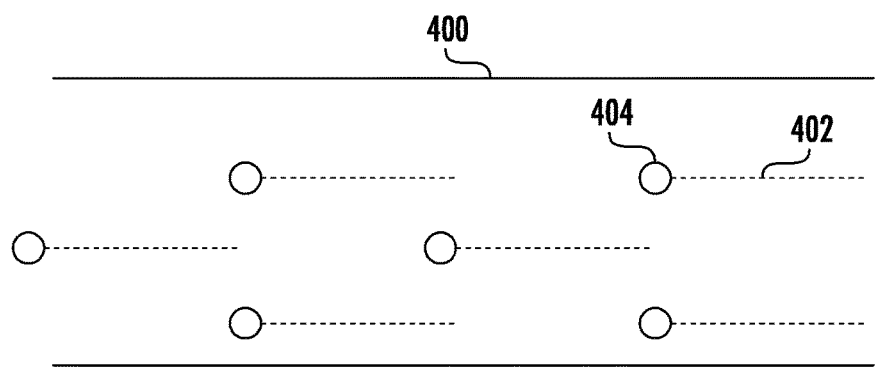
FIG. 23 shows an example embodiment of a outer cover having longitudinal scorelines.

FIG. 23 illustrates a heat-shrink tubing layer 400 that can be placed around the expandable sheaths described herein, according to one embodiment. In some embodiments, the heat-shrink tubing layer 400 can comprise a plurality of cuts or scorelines 402 extending axially along the tubing layer 400 and terminating at distal stress relief features configured as circular openings 404. It is contemplated that the distal stress relief feature can be configured as any other regular or irregular curvilinear shape including, for example, oval and/or ovoid shaped openings. It is also contemplated various shaped distal stress relief features along and around the heat-shrink tubing layer 400. As the delivery apparatus 10 is advanced through the sheath, the heat-shrink tubing layer 400 can split open along the scorelines 402, and the distally positioned openings 404 can arrest further tearing or splitting of the tubing layer along the respective scorelines. As such, the heat-shrink tubing layer 400 remains attached to the sheath along the sheath length. In the illustrated embodiment, the scorelines and associated openings 404 are longitudinally and circumferentially offset from one another or staggered. Thus, as the sheath expands, the scorelines 402 can form rhomboid structures. The scorelines can also extend in other directions, such as helically around the longitudinal axis of the sheath, or in a zig-zag pattern.

In other embodiments, splitting or tearing of the heat-shrink tubing layer may be induced in a variety of other ways, such as by forming weakened areas on the tubing surface by, for example, applying chemical solvents, cutting, scoring, or ablating the surface with an instrument or laser, and/or by decreasing the wall thickness or making cavities in the tubing wall (e.g., by femto-second laser ablation).

Figure 29:
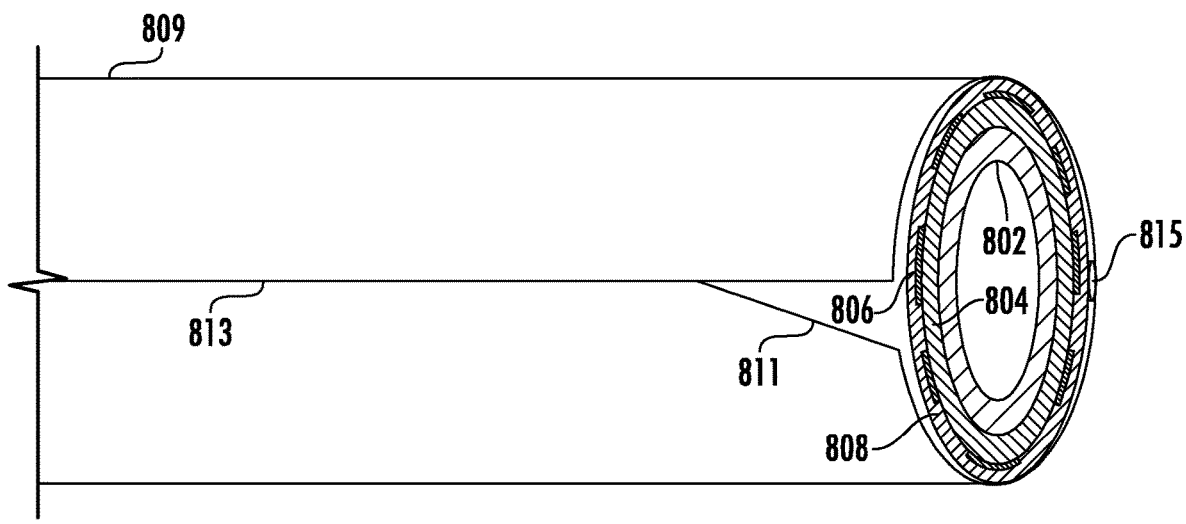
FIG. 29 shows a perspective view of an additional expandable sheath embodiment.
Figure 30:
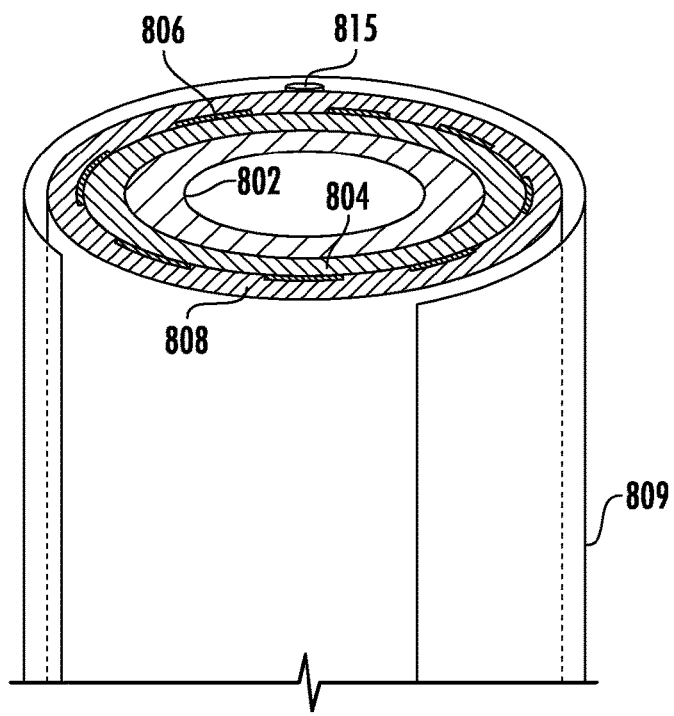
FIG. 30 shows a perspective view of the embodiment of FIG. 29 with the outer heat shrink tubing layer partially torn away from the inner sheath layers.
Figure 31:
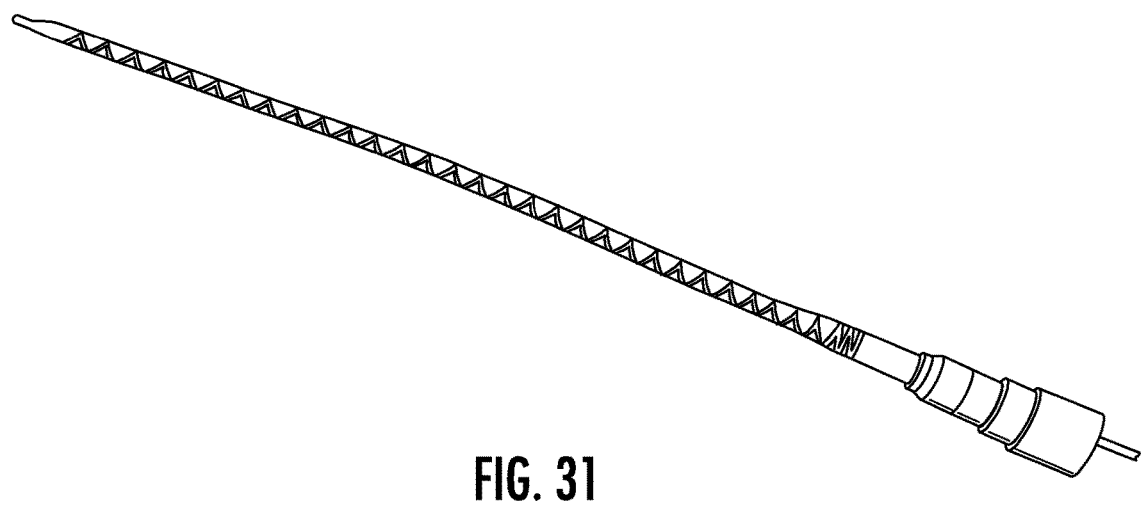
FIG. 31 shows a side view of a sheath embodiment prior to movement of a delivery system therethrough.
Figure 32:
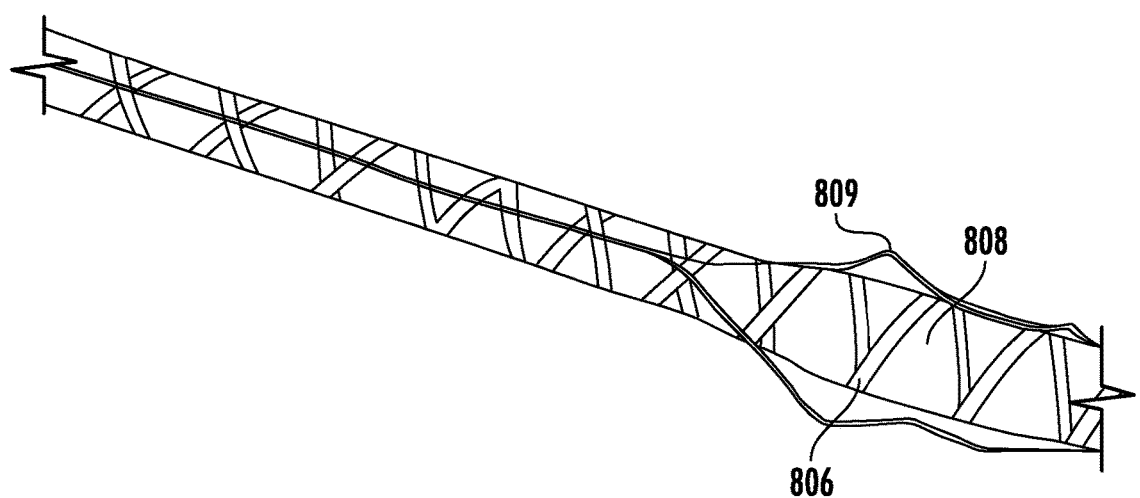
FIG. 32 shows a side view of a sheath embodiment as a delivery system moves through, splitting the heat shrink tubing layer.
Figure 33:
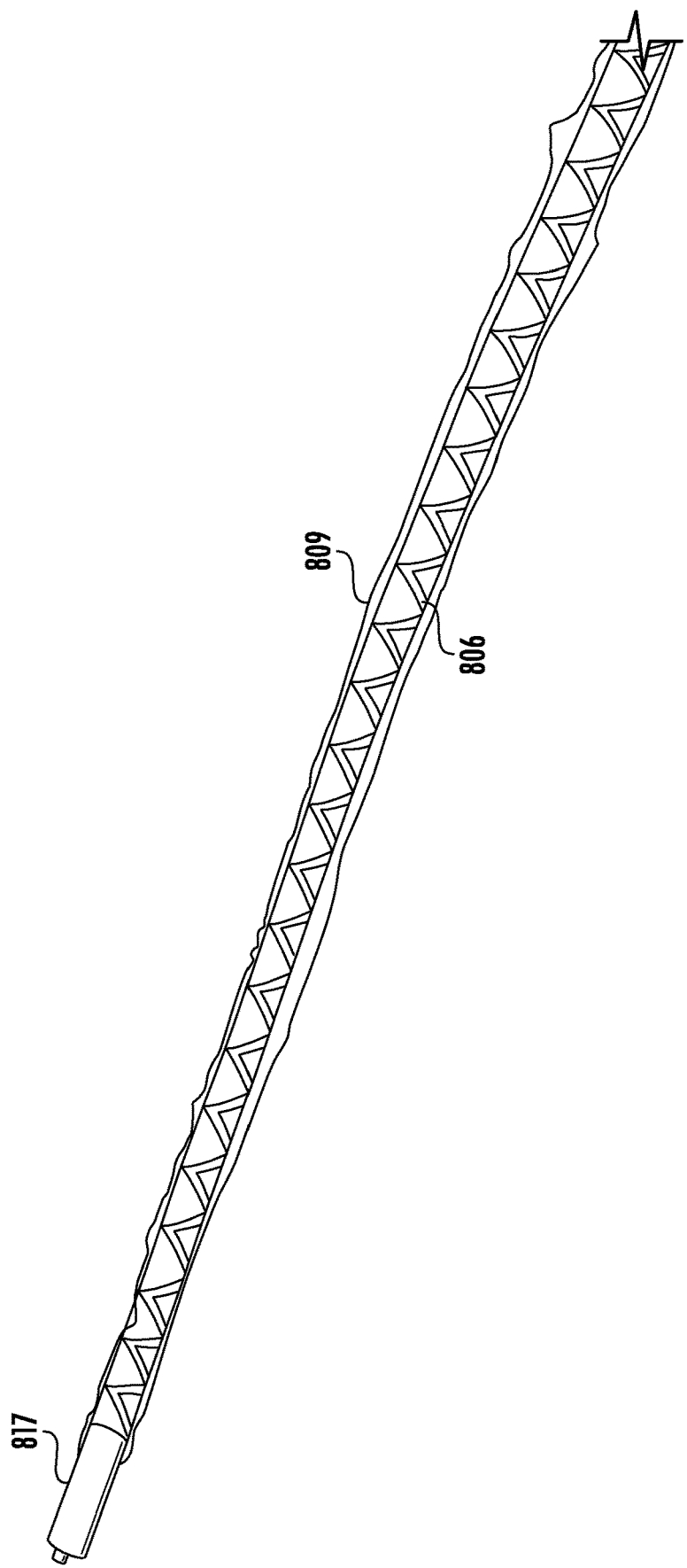
FIG. 33 shows a side view of a sheath embodiment with the delivery system fully moved through, the heat shrink tubing layer fully split along the length of the sheath.

In some embodiments, the heat-shrink tubing layer may be attached to the body of the sheath by adhesive, welding, or any other suitable fixation means. FIG. 29 shows a perspective view of a sheath embodiment including an inner layer 802, a braided layer 804, an elastic layer 806, an outer layer 808, and a heat shrink tubing layer 809. Heat shrink tubing layer 809 includes a split 811 and a perforation 813 extending along the heat shrink tubing layer 809. Heat shrink tubing layer 809 is bonded to the outer layer 808 at an adhesive seam 815. For example, in certain embodiments the heat-shrink tubing layer 809 can be welded, heat-bonded, chemically bonded, ultrasonically bonded, and/or bonded using adhesive agents (including, but not limited to, hot glue, for example LDPE fiber hot glue) at seam 815. The outer layer 808 can be bonded to the heat shrink tubing layer 809 axially along the sheath at a seam 815, or in a spiral or helical fashion. FIG. 30 shows a sheath having a heath shrink tubing layer 809, but prior to movement of a delivery system therethrough. FIG. 32 shows a perspective view of a sheath wherein the heat shrink tubing layer 809 has been partially torn open and detached as a passing delivery system widens the diameter of the sheath. Heat shrink tubing layer 809 is being retained by the adhesive seam 815. Attaching the heat-shrink tubing layer 809 to the sheath in this manner can help to keep the heat-shrink tubing layer 809 attached to the sheath after the layer splits and the sheath has expanded, as shown in FIG. 33, where delivery system 817 has moved completely through the sheath and torn the heat shrink tubing layer 809 along the entire length of the sheath.

In another embodiment, the expandable sheath can have a distal end or tip portion comprising an elastic thermoplastic material (e.g., Pebax), which can be configured to provide an interference fit or interference geometry with the corresponding portion of the vessel dilator 300. In certain configurations, the outer layer of the sheath may comprise polyamide (e.g., nylon) in order to provide for welding the distal end portion to the body of the sheath. In certain embodiments, the distal end portion can comprise a deliberately weakened portion, scoreline, slit, etc., to allow the distal end portion to split apart as the delivery apparatus is advanced through the distal end portion.

In another embodiments, the entire sheath could have an elastomeric outer cover that extends longitudinally from the handle to the distal end portion 140 of the sheath, extending onward to create an overhang similar to overhang 408 shown in FIG. 22. The elastomeric overhang portion conforms tightly to the vessel dilator but remains a part of the sheath once the vessel dilator is removed. As a delivery system is passed through, the elastomeric overhang portion expands and then collapses to allow it to pass. The elastomeric overhang portion, or the entire elastomeric outer cover, can include deliberately weakened portions, scorelines, slits, etc. to allow the distal end portion to split apart as the delivery apparatus is advanced through the distal end portion.

Figure 24:
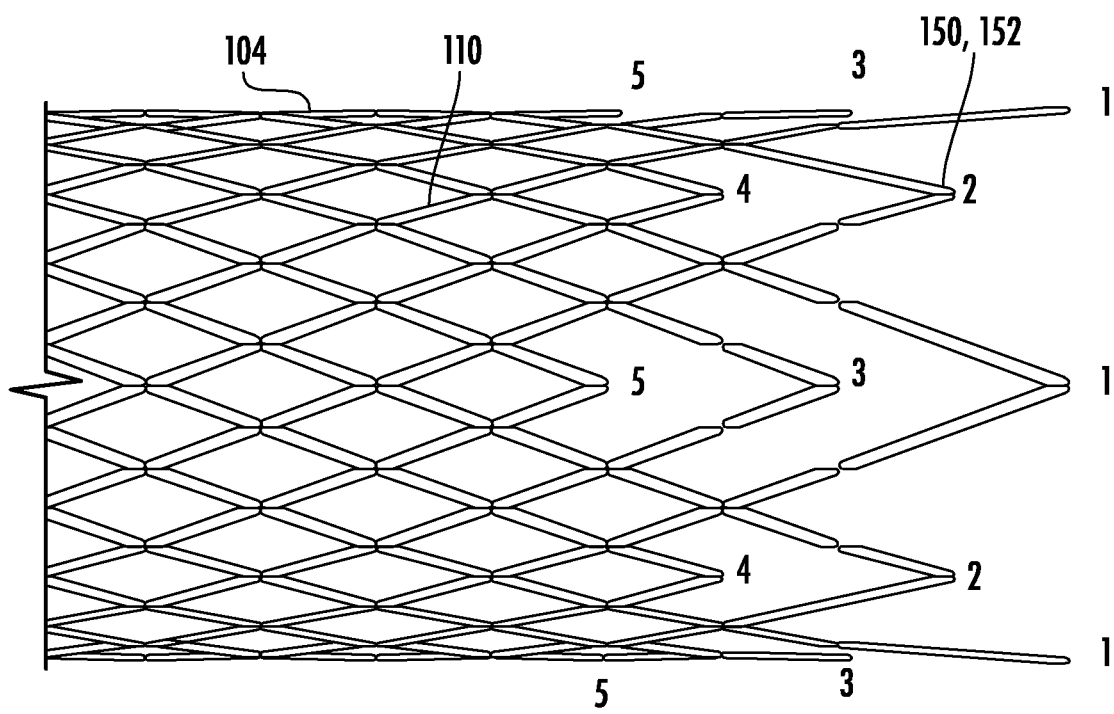
FIG. 24 illustrates an end portion of an embodiment of a braided layer of an expandable sheath.

FIG. 24 illustrates an end portion (e.g., a distal end portion) of another embodiment of the braided layer 104 in which portions 150 of the braided filaments 110 are bent to form loops 152, such that the filaments loop or extend back in the opposite direction along the sheath. The filaments 110 can be arranged such that the loops 152 of various filaments 110 are axially offset from each other in the braid. Moving toward the distal end of the braided layer 104 (to the right in the figure), the number of braided filaments 110 can decrease. For example, the filaments indicated at 5 can form loops 152 first, followed by the filaments indicated at 4, 3, and 2, with the filaments at 1 forming the distal-most loops 152. Thus, the number of filaments 110 in the braid decreases in the distal direction, which can increase the radial flexibility of the braided layer 104.

In another embodiment, the distal end portion of the expandable sheath can comprise a polymer such as Dyneema®, which can be tapered to the diameter of the vessel dilator 300. Weakened portions such as dashed cuts, scoring, etc., can be applied to the distal end portion such that it will split open and/or expand in a repeatable way.

Crimping of the expandable sheath embodiments described herein can be performed in a variety of ways, as described above. In additional embodiments, the sheath can be crimped using a conventional short crimper several times longitudinally along the longer sheath. In other embodiments, the sheath may be collapsed to a specified crimped diameter in one or a series of stages in which the sheath is wrapped in heat-shrink tubing and collapsed under heating.

For example, a first heat shrink tube can be applied to the outer surface of the sheath, the sheath can be compressed to an intermediate diameter by shrinking the first heat shrink tube (via heat), the first heat shrink tube can be removed, a second heat shrink tube can be applied to the outer surface of the sheath, the second heat shrink tube can be compressed via heat to a diameter smaller than the intermediate diameter, and the second heat shrink tube can be removed. This can go on for as many rounds as necessary to achieve the desired crimped sheath diameter.

Crimping of the expandable sheath embodiments described herein can be performed in a variety of ways, as described above. A roller-based crimping mechanism 602, such as the one shown in FIGS. 25A-25C, can be advantageous for crimping elongated structures such as the sheaths disclosed herein. The crimping mechanism 602 has a first end surface 604, a second end surface 605, and a longitudinal axis a-a extending between the first and second end surfaces 604, 605. A plurality of disc-shaped rollers 606a-f are radially arranged about the longitudinal axis a-a, each positioned at least partially between the first and second end surfaces of the crimping mechanism 602. Six rollers are depicted in the embodiment shown, but the number of rollers may vary. Each disc-shaped roller 606 is attached to the larger crimping mechanism by a connector 608. A side cross-sectional view of an individual disc-shaped roller 606 and connector 608 is shown in FIG. 25B, and a top view of an individual disc-shaped roller 606 and connector 608 is shown in FIG. 25C. An individual disc-shaped roller 606 has a circular edge 610, a first side surface 612, a second side surface 614, and a central axis c-c extending between center points of first and second side surfaces 612, 614, as shown in FIG. 25C. The plurality of disc-shaped rollers 606a-f are radially arranged about the longitudinal axis a-a of the crimping mechanism 602 such that each central axis c-c of a disc-shaped roller 606 is oriented perpendicularly to the longitudinal axis a-a of the crimping mechanism 602. The circular edges 610 of the disc-shaped rollers partially define a passage that extends axially through the crimping mechanism 602 along longitudinal axis a-a.

Each disc-shaped roller 606 is held in place in the radially arranged configuration by a connector 608 that is attached to crimping mechanism 602 via one or more fasteners 619, such that the location of each of the plurality of connectors is fixed with respect to the first end surface of the crimping mechanism 602. In the depicted embodiment, fasteners 619 are positioned adjacent an outer portion of the crimping mechanism 602, radially outwardly of the disc-shaped rollers 606. Two fasteners 619 are used to position each connector 608 in the embodiment shown, but the number of fasteners 619 can vary. As shown in FIGS. 25B and 25C, a connector 608 has a first arm 616 and a second arm 618. First and second arms 616, 618 extend over a disc-shaped roller 608 from a radially-outward portion of circular edge 610 to a central portion of the disc-shaped roller 608. A bolt 620 extends through the first and second arms 616, 618 and through a central lumen of the disc-shaped roller 608, the central lumen passing from a center point of front surface 612 to a center point of the back surface 614 of the disc-shaped roller 606 along central axis c-c. The bolt 620 is positioned loosely within the lumen, with substantial clearance/space to allow the disc-shaped roller 608 to rotate about central axis c-c.

During use, an elongated sheath is advanced from the first side 604 of the crimping mechanism 602, through the axial passage between the rollers, and out the second side 605 of the crimping mechanism 602. The pressure from the circular edge 610 of the disc shaped rollers 606 reduces the diameter of the sheath to a crimped diameter as it rolls along the outer surface of the elongated sheath.

Figure 26:
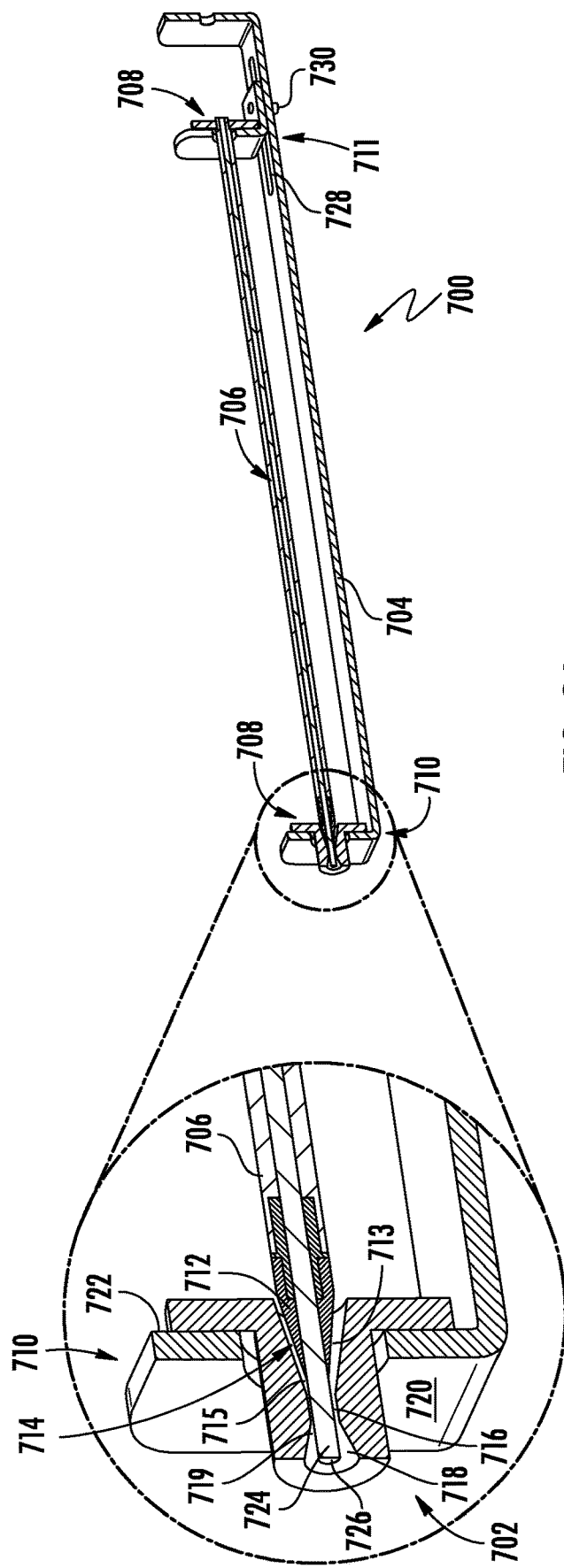
FIG. 26 shows an embodiment of a device for crimping an elongated expandable sheath. The encircled portion of the device is magnified in the inset at the left side of the picture.

FIG. 26 shows an embodiment of a crimping device 700 designed to facilitate crimping of elongated structures, such as sheaths. The crimping device includes an elongated base 704, and elongated mandrel 706 positioned above the elongated base 704, and a holding mechanism 708 attached to the elongated base 704. The holding mechanism 708 supports the mandrel 706 in an elevated position above base 704. The holding mechanism includes a first end piece 710 that includes a crimping mechanism 702. The mandrel 706 includes a conical end portion 712 that nests within a first tapered portion 713 of a narrowing lumen 714 of the first end piece 710. The conical end portion 712 of mandrel 706 is positioned loosely within the narrowing lumen 714, with enough space or clearance between the conical end portion 712 and the lumen 714 to allow for passage of an elongated sheath over the conical end portion 712 of mandrel 706 and through the narrowing lumen 714. During use, the conical end portion 712 helps to avoid circumferential buckling of the sheath during crimping. In some embodiments, the mandrel 706 can also include a cylindrical end portion 724 that extends outwardly from the conical end portion 712 and defines an end 726 of the mandrel 706.

The first tapered portion 713 of the narrowing lumen 714 opens toward a second end piece 711 of the holding mechanism 708, such that the widest side of the taper is located on an inner surface 722 of the first end piece 710. In the embodiment shown, the first tapered portion 713 narrows to a narrow end 715 that connects with a narrow cylindrical portion 716 of the narrowing lumen 714. In this embodiment, the narrow cylindrical portion 716 defines the narrowest diameter of the narrowing lumen 714. The cylindrical end portion 724 of the mandrel 706 may nest loosely within the narrow cylindrical portion 716 of the narrowing lumen 714, with enough space or clearance between the cylindrical end portion 724 and the narrow cylindrical portion 716 of the lumen to allow for passage of the elongated sheath. The elongated nature of the narrow cylindrical portion 716 may facilitate smoothing of the crimped sheath after it has passed over the conical end portion 712 of the mandrel. However, the length of the cylindrical portion 716 of the narrowing lumen 714 is not meant to limit the invention, and in some embodiments, the crimping mechanism 702 may only include first tapered portion 713 of the narrowing lumen 714, and still be effective to crimp an elongated sheath.

At the opposite end of the first end piece 710 shown in FIG. 26, a second tapered portion 718 of the narrowing lumen 714 opens up from narrow cylindrical portion 716 such that the widest side of the taper located on the outer surface 720 of the first end piece 710. The narrow end 719 of the second tapered portion 718 connects with the narrow cylindrical portion 716 of the narrowing lumen 714 in the interior of the crimping mechanism 702. The second tapered portion 718 of the narrowing lumen 714 may not be present in some embodiments.

The holding mechanism 708 further includes a second end piece 711 positioned opposite the elongated base 704 from the first end piece 710. The second end piece 711 is movable with respect to elongated base 704, such that the distance between the first end piece 710 and the second end piece 711 is adjustable and therefore able to support mandrels of varying sizes. In some embodiments, elongated base 704 may include one or more elongated sliding tracks 728. The second end piece 711 can be slidably engaged to the sliding track 728 via at least one reversible fastener 730, such as, but not limited to, a bolt that extends into or through the second end piece 711 and the elongated sliding track 728. To move the second end piece 711, the user would loosen or remove the reversible fastener 730, slide the second end piece 711 to the desired location, and replace or tighten the reversible fastener 730.

In use, a sheath in an uncrimped diameter can be placed over the elongated mandrel 706 of the crimping device 700 shown in FIG. 26, such that the inner surface of the entire length of the uncrimped sheath is supported by the mandrel. The uncrimped sheath is then advanced over the conical end portion 712 and through the narrowing lumen 714 of the crimping mechanism 702. The uncrimped sheath is crimped to a smaller, crimped diameter via pressure from the interior surface of the narrowing lumen 714. In some embodiments, the sheath is advanced through both a first tapered portion 713 and a cylindrical portion 716 of the narrowing lumen 714 before exiting the crimping mechanism 702. In some embodiments, the sheath is advanced through a first tapered portion 713, a cylindrical portion 716, and a second tapering portion 718 of the narrowing lumen 714 before exiting the crimping mechanism 702.

Figure 25A:
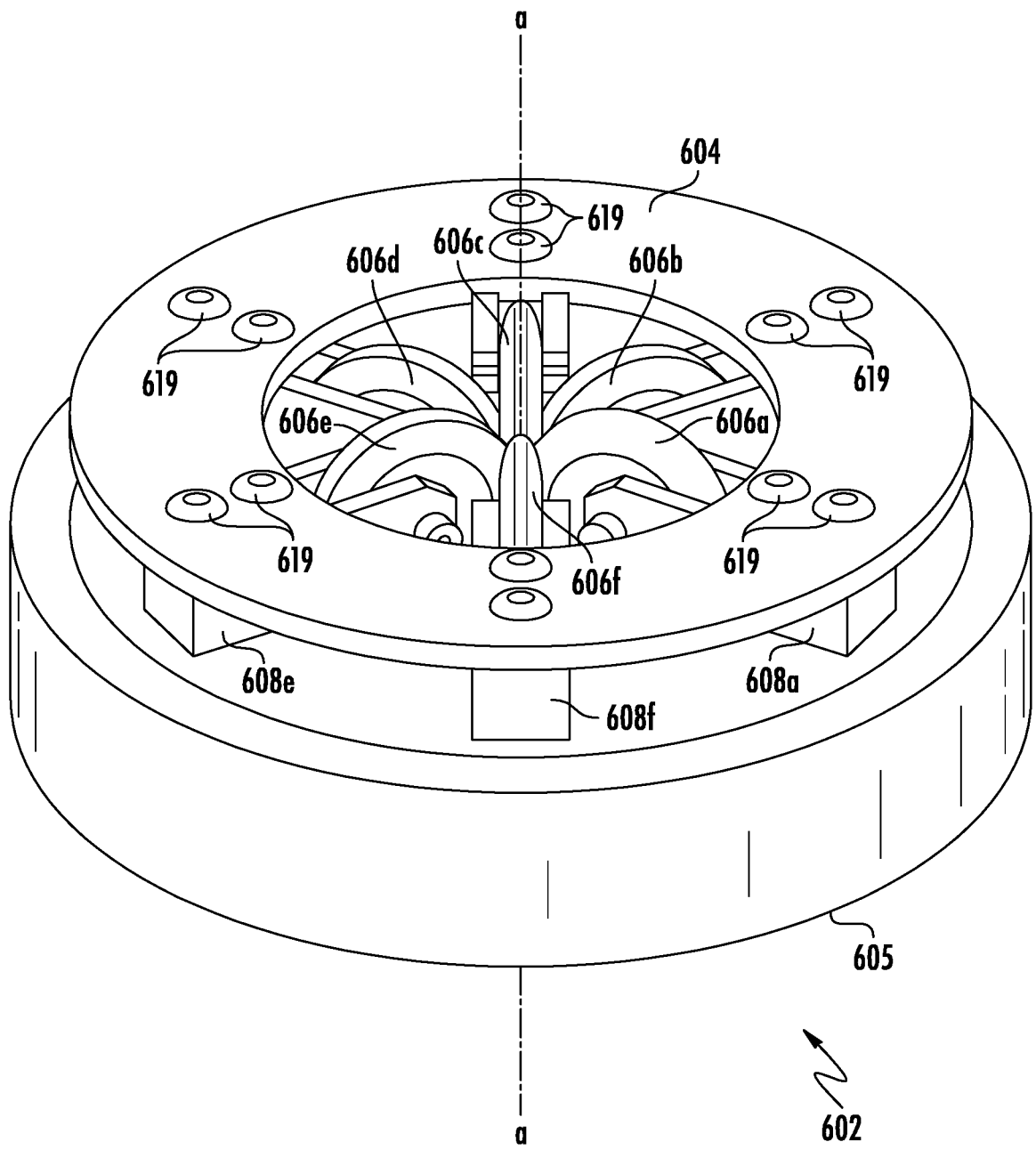
FIG. 25A illustrates a perspective view of a roller-based crimping mechanism embodiment for crimping an expandable sheath.
Figure 25B:
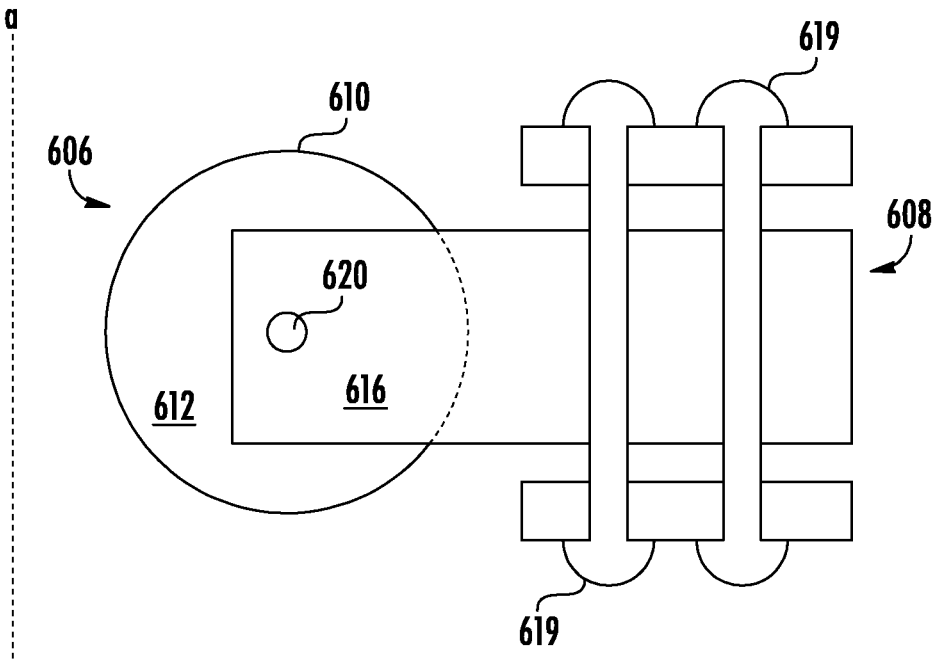
FIG. 25B illustrates a side view of a disc-shaped roller and connector of the crimping mechanism shown in FIG. 25A.
Figure 25C:
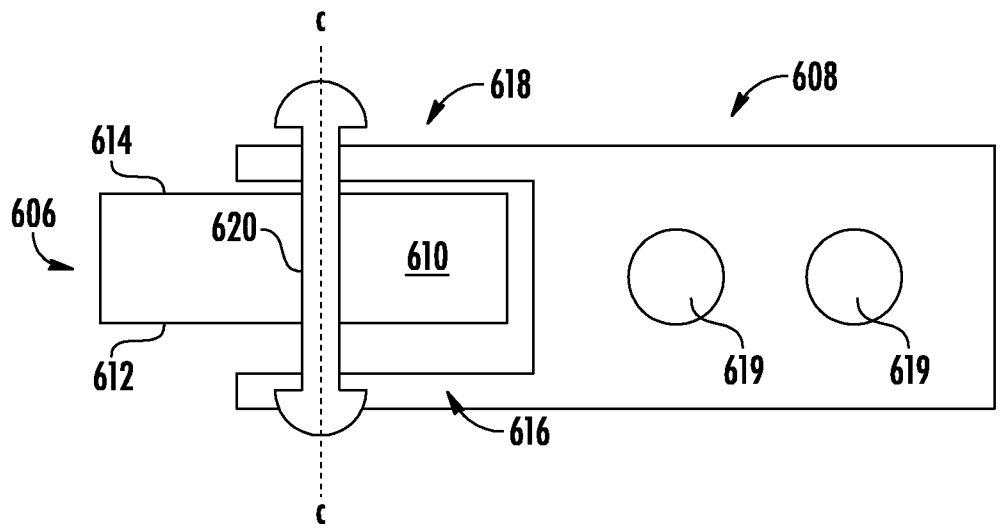
FIG. 25C illustrates a top view of a disc-shaped roller and connector of the crimping mechanism shown in FIG. 25A.

In some embodiments, the crimping mechanism 602 shown in FIG. 25A may be positioned within a larger crimping device such as crimping device 700 shown in FIG. 26. For example, the crimping mechanism 602 can be positioned within the first end piece 710 of crimping device 700 instead of, or in combination with, crimping mechanism 702. For example, the rolling crimping mechanism 602 could entirely replace the narrowing lumen 714 of crimping mechanism 702, or the rolling crimping mechanism 602 could be nested within the narrow cylindrical portion 716 of the narrowing lumen 714 of the crimping mechanism 702, such that the first tapered portion 713 feeds the expandable sheath through the plurality of radially arranged disc-shaped rollers 606.

Figure 34:
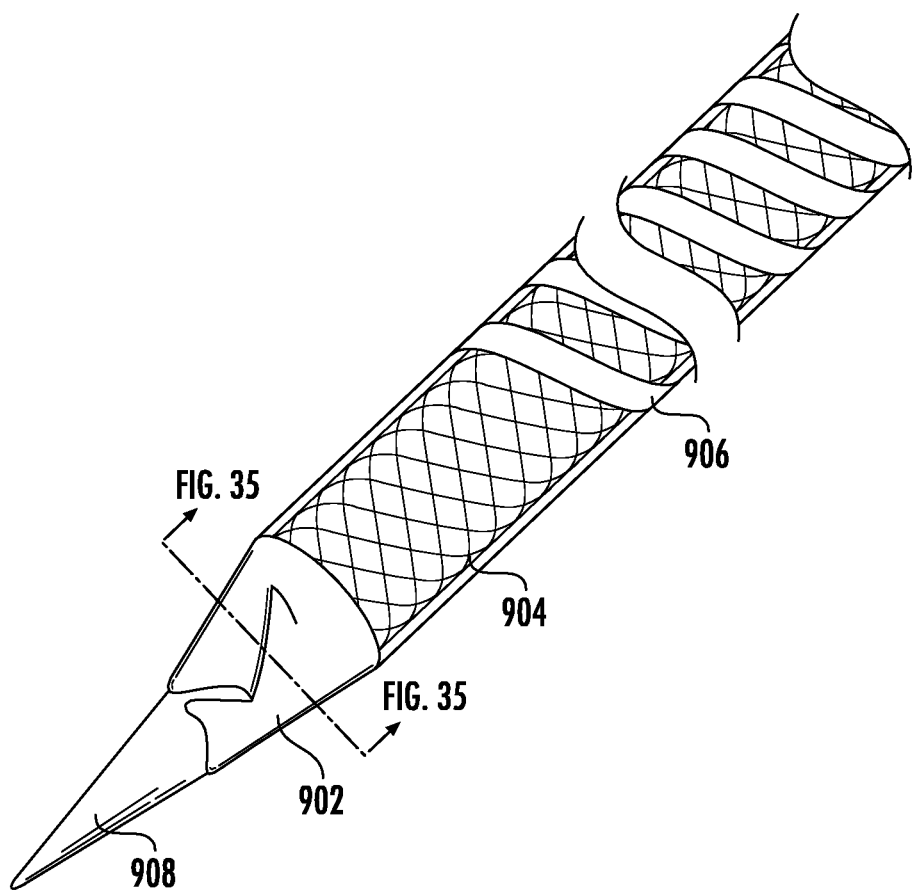
FIG. 34 shows a perspective view of a sheath embodiment having a distal end portion folded around an introducer.
Figure 35:
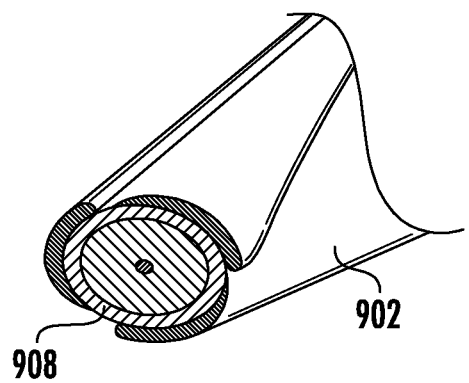
FIG. 35 shows an enlarged, cross sectional view of the distal end portion folded around the introducer.

FIGS. 34-36 show a sheath embodiment including a distal end portion 902, which can be an extension of an outer cover extending longitudinally along the sheath in the proximal direction. FIG. 34 shows a distal end portion 902 folded around an introducer (in the crimped and collapsed configuration). FIG. 35 shows a cross section of the distal end portion 902 folded around the introducer 908 (in the crimped and collapsed configuration). FIG. 36 shows the distal end portion 902 after being opened by a passing delivery system. The distal end portion 902 can be formed of, for example, one or more layers of a similar or the same material used to form the outer layer of the sheath. In some embodiments, the distal end portion 902 includes an extension of the outer layer of the sheath, with or without one more additional layers added by separate processing techniques. The distal end portion can include anywhere from 1 to 8 layers of material (including 1, 2, 3, 4, 5, 6, 7, and 8 layers of material). In some embodiments, the distal end portion comprises multiple layers of a Dyneema® material. The distal end portion 902 can extend distally beyond a longitudinal portion of the sheath that includes braided layer 904 and elastic layer 906. In fact, in some embodiments, the braided layer 904 may extend distally beyond the elastic layer 906, and the distal end portion 902 may extend distally beyond both the braided layer 904 and elastic layer 906, as shown in FIGS. 34-36.

The distal end portion 902 may have a smaller collapsed diameter than the more proximal portions of the sheath, giving it a tapered appearance. This smooths the transition between the introducer/dilator and the sheath, ensuring that the sheath does not get lodged against the tissue during insertion into the patient. The smaller collapsed diameter can be a result of multiple folds (for example, 1, 2, 3, 4, 5, 6, 7, or 8 folds) positioned circumferentially (evenly or unevenly spaced) around the distal end portion. For example, a circumferential segment of the distal end portion can be brought together and then laid against the adjacent outer surface of the distal end portion to create an overlapping fold. In the collapsed configuration, the overlapping portions of the fold extend longitudinally along the distal end portion 902. Exemplary folding methods and configurations are described in U.S. application Ser. No. 14/880,109 and U.S. application Ser. No. 14/880,111, each of which are hereby incorporated by reference in their entireties. Scoring can be used as an alternative, or in addition to folding of the distal end portion. Both scoring and folding of the distal end portion 902 allow for the expansion of the distal end portion upon the passage of the delivery system, and ease the retraction of the delivery system back into the sheath once the procedure is complete.

In some embodiments, a distal end portion can be added, the sheath and tip can be crimped, and the crimping of the distal end portion and sheath can be maintained, by the following method. As mentioned above, the distal end portion 902 can be an extension of the outer layer of the sheath. It can also be a separate, multilayer tubing that is heat bonded to the remainder of the sheath prior to the tip crimping processing steps. In some embodiments, the separate, multilayer tubing is heat bonded to a distal extension of the outer layer of the sheath to form the distal end portion 902. For crimping of the sheath after tip attachment, the sheath is heated on small mandrel. The distal end portion 902 can be folded around the mandrel to create the folded configuration shown in FIG. 34. The folds be added to the distal end portion 902 prior to the tip crimping process, or at an intermediate point during the tip crimping process. In some embodiments, the small mandrel can be from about 2 millimeters to about 4 millimeters in diameter (including about 2.2 millimeters, about 2.4 millimeters, about 2.6 millimeters, about 2.8 millimeters, about 3.0 millimeters, about 3.2 millimeters, about 3.4 millimeters, about 3.6 millimeters, about 3.8 millimeters and about 4.0 millimeters). The heating temperature will be lower than the melting point of the material used. This can cause the material to shrink on its own to a certain extent. For example, in some embodiments, such as those where Dyneema® materials are utilized as part of the sheath outer layer and/or distal end portion materials, a sheath crimping process begins by heating the sheath on a 3 millimeter mandrel to about 125 degrees Celsius (lower than Dyneema® melting point of about 140 degrees Celsius). This causes the sheath to crimp itself to about a 6 millimeter outer diameter. At this point, the sheath and distal end region 902 are allowed to cool. A heat shrink tube can then be applied. In some embodiments, the heat shrink tube can have a melting point that is about the same as the melting point of the distal end portion material. The sheath with the heat shrink tube extending over the sheath and the distal end portion 902 is heated again (for example, to about 125 degrees Celsius for sheaths including Dyneema® outer layers and distal end portions), causing the sheath to crimp to an even smaller diameter. At the distal end portion 902, a higher temperature can be applied (for example, from about 145 degrees Celsius to about 155 degrees Celsius for Dyneema® material) causing the layers of material to melt together in the folded configuration shown in FIG. 34 (the folds can be added at any point during this process). The bonds at the distal end portion 902 induced by the high temperature melting step will still be weak enough to be broken by a passing delivery system. As a final step, the heat shrink tube is removed, and the shape of the sheath remains at the crimped diameter.

Embodiments of the sheaths described herein may comprise a variety of lubricious outer coatings, including hydrophilic or hydrophobic coatings, and/or surface blooming additives or coatings.

Figure 27:
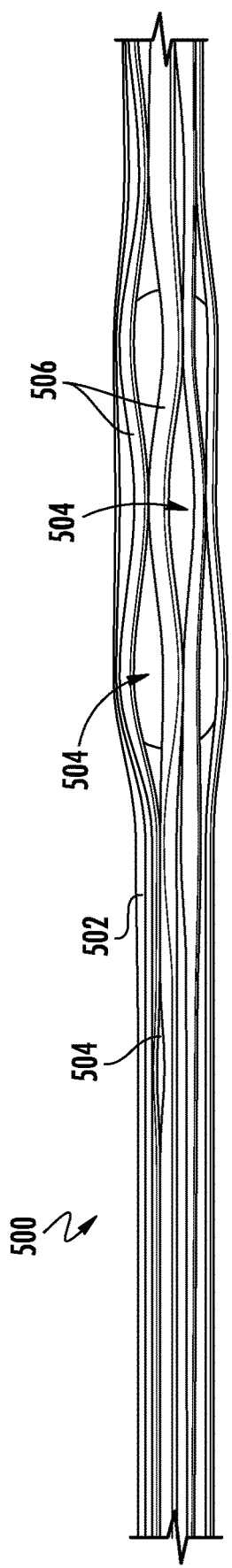
FIG. 27 shows an embodiment of an expandable sheath having an inner layer with scorelines.

FIG. 27 illustrates another embodiment of a sheath 500 comprising a tubular inner layer 502. The inner layer 502 may be formed from an elastic thermoplastic material such as nylon, and can comprise a plurality of cuts or scorelines 504 along its length such that the tubular layer 502 is divided into a plurality of long, thin ribs or portions 506. When the delivery apparatus 10 is advanced through the tubular layer 502, the scorelines 504 can resiliently expand or open, causing the ribs 506 to splay apart, and allowing the diameter of the layer 502 to increase to accommodate the delivery apparatus.

In other embodiments, the scorelines 504 can be configured as openings or cutouts having various geometrical shapes, such as rhombuses, hexagons, etc., or combinations thereof. In the case of hexagonal openings, the openings can be irregular hexagons with relatively long axial dimensions to reduce foreshortening of the sheath when expanded.

The sheath 500 can further comprise an outer layer (not shown), which can comprise a relatively low durometer, elastic thermoplastic material (e.g., Pebax, polyurethane, etc.), and which can be bonded (e.g., by adhesive or welding, such as by heat or ultrasonic welding, etc.) to the inner nylon layer. Attaching the outer layer to the inner layer 502 can reduce axial movement of the outer layer relative to the inner layer during radial expansion and collapse of the sheath. The outer layer may also form the distal tip of the sheath.

Figure 28:
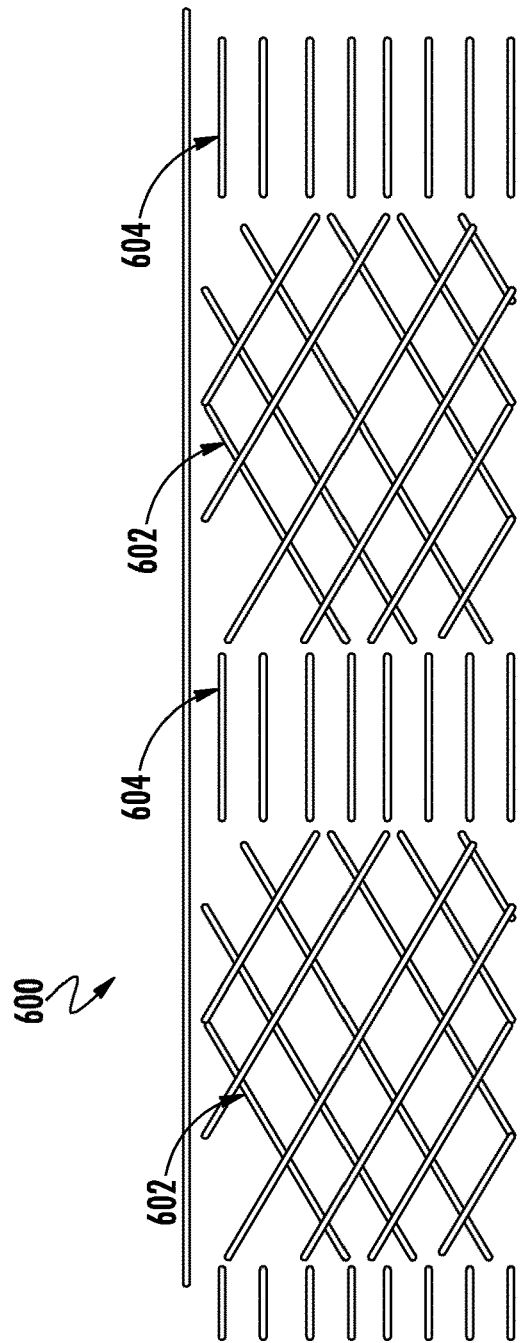
FIG. 28 shows an additional embodiment of a braided layer of an expandable sheath.

FIG. 28 illustrates another embodiment of a braided layer 600 that can be used in combination with any of the sheath embodiments described herein. The braided layer 600 can comprise a plurality of braided portions 602, in which filaments of the braided layer are braided together, and unbraided portions 604, in which the filaments are not braided, and extend axially without being intertwined. In certain embodiments, the braided portions 602 and unbraided portions 604 can alternate along the length of the braided layer 600, or may be incorporated in any other suitable pattern. The proportion of the length of the braided layer 600 given to braided portions 602 and unbraided portions 604 can allow the selection and control of the expansion and foreshortening properties of the braided layer.

In some embodiments, the distal end portion of the sheath (and/or of the vessel dilator) can decrease from the initial diameter of the sheath (e.g., 8 mm) to 3.3 mm (10F), and may decrease to the diameter of a guide wire, allowing the sheath and/or the vessel dilator 300 to run on a guide wire.

General Considerations

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

In the context of the present application, the terms "lower" and "upper" are used interchangeably with the terms "inflow" and "outflow", respectively. Thus, for example, the lower end of a valve is its inflow end and the upper end of the valve is its outflow end.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device toward the user, while distal motion of the device is motion of the device away from the user. The terms "longitudinal" and "axial" refer to an axis extending in the proximal and distal directions, unless otherwise expressly defined.

Unless otherwise indicated, all numbers expressing dimensions, quantities of components, molecular weights, percentages, temperatures, forces, times, and so forth, as used in the specification or claims, are to be understood as being modified by the term "about." Accordingly, unless otherwise indicated, implicitly or explicitly, the numerical parameters set forth are approximations that can depend on the desired properties sought and/or limits of detection under test conditions/methods familiar to those of ordinary skill in the art. When directly and explicitly distinguishing embodiments from discussed prior art, the embodiment numbers are not approximates unless the word "about" is recited. Furthermore, not all alternatives recited herein are equivalents.

In view of the many possible embodiments to which the principles of the disclosed technology may be applied, it should be recognized that the illustrated embodiments are only preferred examples and should not be taken as limiting the scope of the disclosure. Rather, the scope of the disclosure is at least as broad as the following claims. We therefore claim all that comes within the scope and spirit of these claims

The invention claimed is:

1. An expandable sheath for deploying a medical device, comprising:
    a first polymeric layer;
    a braided layer radially outward of the first polymeric layer, the braided layer comprising a plurality of filaments braided together;
    a resilient elastic layer radially outward of the braided layer, the elastic layer being configured to apply radial force to the braided layer and the first polymeric layer; and
    a second polymeric layer radially outward of the elastic layer and bonded to the first polymeric layer such that the braided layer and the elastic layer are encapsulated between the first and second polymeric layers;
    wherein the plurality of filaments of the braided layer are movable between the first and second polymeric layers such that the braided layer is configured to radially expand as a medical device is passed through the sheath; and
    wherein when the medical device is passed through the sheath, the diameter of the sheath expands from a first diameter to a second diameter around the medical device while the first and second polymeric layers resist axial elongation of the sheath such that a length of the sheath remains substantially constant; and
    wherein the sheath resiliently returns to the first diameter by radial force applied by the elastic layer upon passage of the medical device.

2. The expandable sheath of claim 1, wherein:
    the first and second polymeric layers comprise a plurality of longitudinally-extending folds when the sheath is at the first diameter.

3. The expandable sheath of claim 2, wherein the longitudinally extending folds create a plurality of circumferentially spaced ridges and a plurality of circumferentially spaced valleys.

4. The expandable sheath of claim 3, wherein, as a medical device is passed through the sheath, the ridges and valleys level out to allow the sheath to radially expand.

5. The expandable sheath of claim 1, wherein the elastic layer comprises one or more elastic bands helically wound over the braided layer.

6. The expandable sheath of claim 5, wherein the elastic layer comprises two elastic bands wound with opposite helicity.

7. The expandable sheath of claim 1, wherein the filaments of the braided layer are not engaged or adhered to the first or second polymeric layers.

8. The expandable sheath of claim 1, wherein the filaments of the braided layer are resiliently buckled when the sheath is at the first diameter.

9. The expandable sheath of claim 8, wherein the first and second polymeric layers are attached to each other at a plurality of open spaces between the filaments of the braided layer.

10. The expandable sheath of claim 1, further comprising one or more longitudinally extending cords attached to the braided layer.

11. The expandable sheath of claim 1, further comprising an outer cover extending longitudinally beyond distal ends of the first polymeric layer, the braided layer, the elastic layer, and the second polymeric layer to form an overhang.

12. The expandable sheath of claim 11, wherein the outer cover comprises one or more longitudinally extending slits, weakened portions, or scorelines.

13. The expandable sheath of claim 11, wherein the outer cover is formed of a heat-shrink material.

14. The expandable sheath of claim 11, wherein the outer cover is elastomeric.

15. An assembly, comprising:
    the expandable sheath of claim 1, further comprising a distal end portion resiliently expandable between the first diameter and a second diameter;
    a vessel dilator disposed within the sheath, the vessel dilator comprising a tapered nose cone and a retaining member that extends at least partially over the distal end portion of the sheath and is configured to retain the distal end portion of the sheath at the first diameter.

16. The assembly of claim 15, wherein the distal end portion is heat-set toward an expanded configuration, and the elastic layer of the sheath terminates proximally of the distal end of the sheath.

17. The assembly of claim 15, wherein a distal end portion of the braided layer is heat-set toward a flared configuration.

18. The assembly of claim 15, wherein the retaining member is a polymeric heat-shrink layer.

19. The assembly of claim 15, wherein the retaining member is elastomeric and configured to compress the distal end portion of the sheath.

20. The assembly of claim 15, wherein the retaining member is glued or fused to the sheath.

21. The assembly of claim 15, wherein the retaining mechanism comprises a shaft disposed between the dilator and the sheath, the shaft comprising a releasable coupling that mechanically engages both the dilator and the sheath and is configured to be manually deactivated.

22. The assembly of claim 15, wherein the retaining mechanism comprises one or more balloons disposed between the dilator and the sheath.

23. The device of claim 1, wherein at least a portion of the plurality filaments of the braided layer form loops at a distal end of the braided layer.

24. The device of claim 23, wherein the loops are axially offset from each other in the braid.

25. The device of claim 1, wherein the number of the braided filaments decreases toward a distal end of the braided layer.

26. An expandable sheath for deploying a medical device, comprising:
    a first polymeric layer;
    a braided layer radially outward of the first polymeric layer, the braided layer comprising a plurality of filaments braided together and wherein at least portion of the plurality filaments of the braided layer form loops at a distal end of the braided layer;
    a resilient elastic layer radially outward of the braided layer, the elastic layer being configured to apply radial force to the braided layer and the first polymeric layer; and
    a second polymeric layer radially outward of the elastic layer and bonded to the first polymeric layer such that the braided layer and the elastic layer are encapsulated between the first and second polymeric layers;
    wherein when a medical device is passed through the sheath, the diameter of the sheath expands from a first diameter to a second diameter around the medical device while the first and second polymeric layers resist axial elongation of the sheath such that a length of the sheath remains substantially constant; and
    wherein the sheath resiliently returns to the first diameter by radial force applied by the elastic layer upon passage of the medical device.

27. The expandable sheath of claim 1, wherein the second polymeric layer extends to a distal end of the sheath.

28. The expandable sheath of claim 26, wherein the second polymeric layer extends to a distal end of the sheath.

\* \* \* \* \*